(12) United States Patent
Nishino et al.

(10) Patent No.: US 8,153,974 B2
(45) Date of Patent: Apr. 10, 2012

(54) ELECTRONIC DEVICE FOR MINIMIZING LASER LIGHT LEAKAGE

(75) Inventors: Naoyuki Nishino, Ashigarakami-gun (JP); Yasunori Ohta, Ashigarakami-gun (JP); Eiichi Kito, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 613 days.

(21) Appl. No.: 12/320,506

(22) Filed: Jan. 28, 2009

(65) Prior Publication Data
US 2009/0278047 A1 Nov. 12, 2009

(30) Foreign Application Priority Data
Jan. 30, 2008 (JP) ................................. 2008-019758

(51) Int. Cl.
*G01J 5/00* (2006.01)
(52) U.S. Cl. .................................................. 250/338.1
(58) Field of Classification Search ................ 250/338.1
See application file for complete search history.

(56) References Cited

FOREIGN PATENT DOCUMENTS
| JP | 0533119 U | * | 4/1993 |
| JP | B 3494683 | | 6/1995 |
| JP | 2007-60233 | | 3/2007 |
| JP | A 2007-81134 | | 3/2007 |

OTHER PUBLICATIONS

VoIP Deployment Consortium, (http://www.telesa.or.jp/committee/viop/pdf/0507_IPCall_protocol_ver1.pdf) May 2005.
KDDI R&D Laboratories, "The Realization of Infrared Wireless Communications at a Transmission Speed of 1Gbit/s Using a Mobile Telephone" Internet: <URL:http://www.kddilabs.jp/press/img/83_1.pdf> (viewed Jan. 21, 2008).

* cited by examiner

*Primary Examiner* — Mark R Gaworecki
(74) *Attorney, Agent, or Firm* — SOLARIS Intellectual Property Group, PLLC

(57) ABSTRACT

A transportable electronic cassette and an image reading device carry out communication by laser light between themselves, with the separation distance to the casing of the opposing device detected by separation distance sensors provided respectively to the electronic cassette and the image reading device. The value of the separation distance detected is monitored to see whether or not the separation distance exceeds a reference value of the detected value at the start of communication by a specific value or more. Conclusion can be made that there has been a relatively large change in the relative position of the electronic cassette and the image reading device if the detected value of the separation distance becomes greater than the reference value by the specific value or more, and consequently emission is halted of the laser light from the electronic cassette and the image reading device.

20 Claims, 16 Drawing Sheets

FIG. 7A

RELATIVE POSITION AT START OF DATA TRANSFER

SEPARATION DISTANCE DETECTION VALUE L→
REFERENCE VALUE L ref

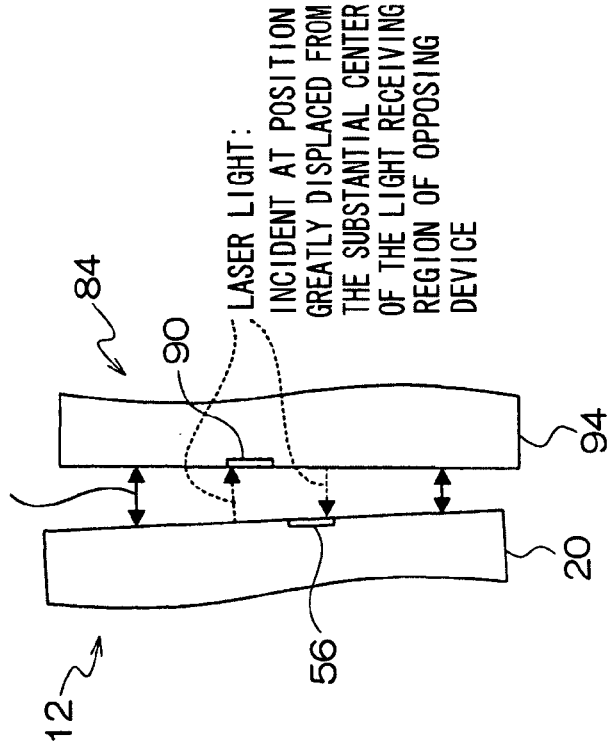

LASER LIGHT:
INCIDENT ON
SUBSTANTIALLY
CENTER OF LIGHT
RECEIVING REGION
OF OPPOSING DEVICE

FIG. 7B

WHEN RELATIVE POSITION CHANGED

SEPARATION DISTANCE DETECTION VALUE L≥L ref+α →
HALT COMMUNICATION

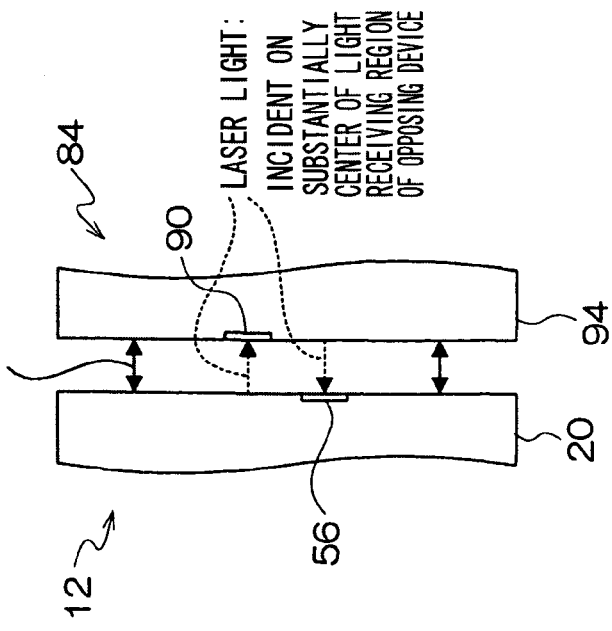

LASER LIGHT:
INCIDENT AT POSITION
GREATLY DISPLACED FROM
THE SUBSTANTIAL CENTER
OF THE LIGHT RECEIVING
REGION OF OPPOSING
DEVICE

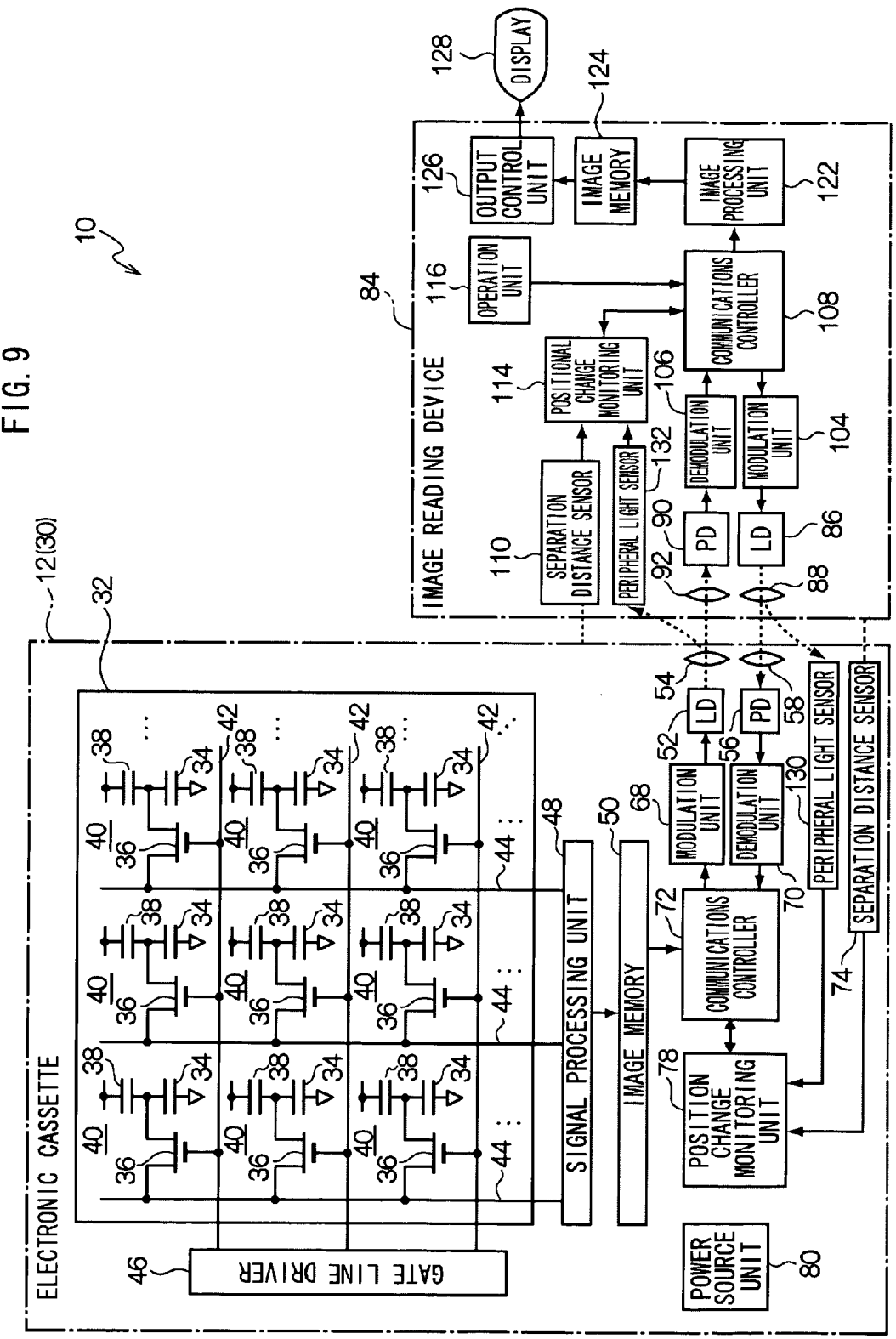

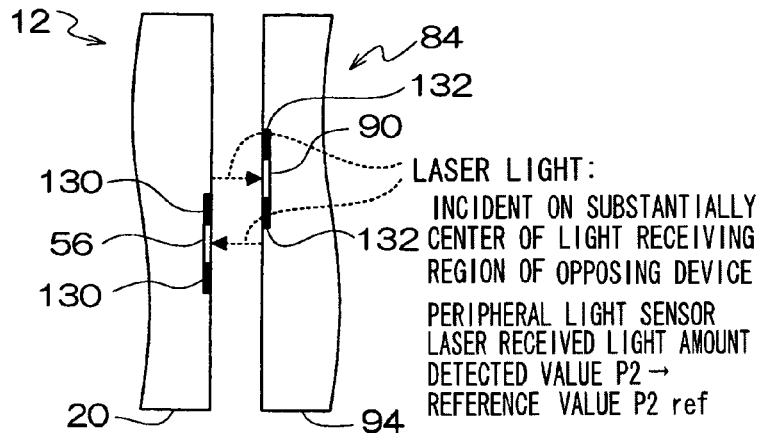
FIG. 12A RELATIVE POSITION AT START OF DATA TRANSFER
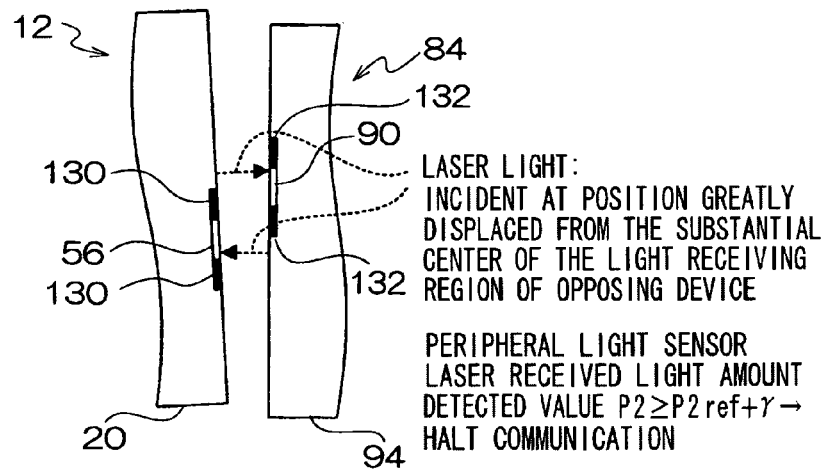
FIG. 12B WHEN RELATIVE POSITION CHANGED
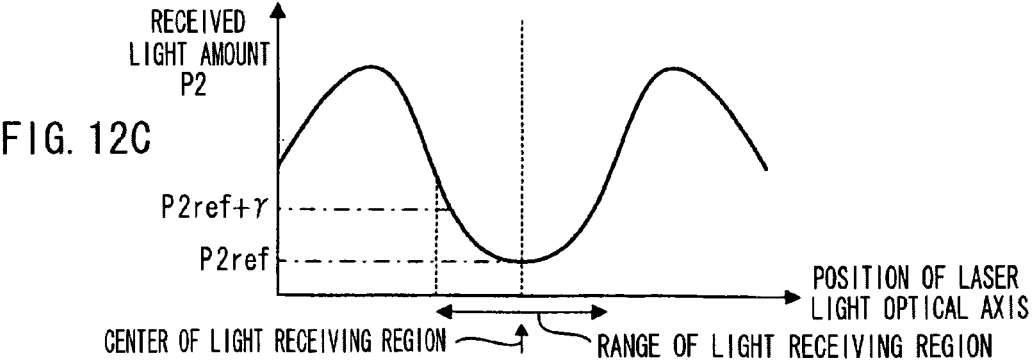
FIG. 12C RELATIONSHIP BETWEEN POSITION OF LASER LIGHT OPTICAL AXIS AND RECEIVED LIGHT AMOUNT OF PERIPHERAL LIGHT SENSOR

ELECTRONIC DEVICE FOR MINIMIZING LASER LIGHT LEAKAGE

CROSS-REFERENCE TO RELATED APPLICATION

This application claims priority under 35 USC 119 from Japanese Patent Application No. 2008-19758, the disclosure of which is incorporated by reference herein.

BACKGROUND OF THE INVENTION

1. Field of the Invention

The present invention relates to an electronic device, and in particular relates to an electronic device that transmits and receives information to and from an opposing device by means of laser light modulated according to the transmission information.

2. Description of the Related Art

Recently technologies have been proposed for realizing wireless communication at extremely high transmission speeds (for example 1 Gb/s) using laser light in the infrared wavelength region (KDDI R&D Laboratories, "The Realization of Infrared Wireless Communications at a Transmission Speed of 1 Gbit/s Using a Mobile Telephone" Internet: <URL:http://www.kddilabs.jp/press/img/83_1.pdf>, (viewed Jan. 21, 2008)). The expectation is that when transmitting data between given electronic devices by application of this technology it should be possible to complete the transmission of a large amount of data within a short period of time, even if one or more of the electronic devices is transportable and a large amount of data is to be transmitted, enabling a large reduction in communication time of wireless communication between existing electronic devices. Consequently, transmission by wireless communication of large amounts of data between devices, which would have been inconceivable using known wireless communications, is expected to be realizable, along with various other applications.

For example, in Published Japanese Patent No. 349683 a cassette for radiation detection (also called an electronic cassette) is described configured with an inbuilt radiation detection device and image memory. Radiographic images detected by the radiation detection device are stored as image data in the image memory, and image data read out from the image memory is converted into a wireless signal and output to an external signal processing circuit. In the medical field many devices are preferably not placed in an environment in which electromagnetic waves are radiating. Up to now, preferable wireless communications for the above cassette have been limited, such as to infrared communication based on IrDA (Infrared Data Association) standards, and the like. However, in such types of medical equipment, while the communication speed of infrared communication based on IrDA standards is about 115 kb/s to 6 Mb/s, a low compression ratio is selected when image data is reversibly compressed, in order to avoid any adverse effect on the interpretation of radiograms. This results in image data transfer taking an extremely long period of time. In contrast, if the above described communication by laser light could be applied for wireless communication in the above cassette, a great reduction in the duration of image data transfer could be realized.

In Japanese Patent Application Laid-Open (JP-A) No. 2007-81134 related to the above, an optical communication module is configured with a laser diode provided to a lead frame, and configured with a transparent resin section, as an adjusting means for spreading out the light output distribution of the laser diode and adjusting the output thereof. The transparent resin section is configured with a transparent resin, for encapsulating the laser diode, and containing glass filler exhibiting an ability to transmit and disperse light. The glass filler is added to the transparent resin and substantially uniformly distributed within the whole of the transparent resin.

In a mode in which wireless communication is carried out using laser light between electronic devices, if one or more of the electronic devices is transportable then the wireless communication is carried out in a state in which the two electronic devices are disposed in a positional relationship enabling wireless communication. However, since one or more of the electronic devices is transportable, if the casing of the electronic device is imparted with a pressing force, vibration or the like during communication with the laser light, the relative position of the two electronic devices changes, and there is a possibility of this leading to laser light leakage from the space interposed between the two electronic devices.

In order to address this issue, the technology of JP-A No. 2007-81134 is a technology that realizes a spreading out of the light output distribution of the optical communication module and a reduction in the light output amount of the optical communication module by repeatedly diffracting light from the laser diode using the glass filler. There is no consideration given in this technology to laser light leakage when the relative position of the electronic devices has changed during communication by laser light.

SUMMARY OF THE INVENTION

In consideration of the above circumstances, the present invention provides a electronic device capable of ensuring safety when there has been a change in the relative position with respect to an opposing device during transmission or receiving of information to or from the opposing device using laser light.

An electronic device according to a first aspect embodiment of the present invention includes: a receiving device, receiving transmission information from an opposing device by detecting laser light emitted from the opposing device, the opposing device provided with a first emission unit for emitting laser light and with a first modulating unit for modulating the laser light emitted from the first emission unit according to the transmission information, and by demodulating the transmission information from the detection result of the laser light; a separation distance detection unit, determining whether or not there has been a change in the separation distance to the opposing device of a threshold value or above; and a first control unit, issuing a warning or halting emission of the laser light from the opposing device when determination is made by the separation distance detection unit that the separation distance to the opposing device has changed by the threshold value or above.

In the first aspect of the present invention, the opposing device is provided with functionality for emitting laser light modulated according to the transmission information, and the relative position of the casing of the opposing device to the casing of the device itself, i.e., the electronic device, is in an adjusted state to a position enabling communication with the laser light emitted from the opposing device incident within the light receiving region provided on an outer face of the casing of the device itself, and the receiving device detects the laser light irradiated within the light receiving region. The device itself receives the transmission information from the opposing device by demodulating the transmission information from the laser light detection result. In the adjusted state, of the relative position of the casing of the opposing device to the casing of the device itself, to a position enabling communication, if the device itself and/or the opposing device is imparted with a pressing force, vibration or the like during the period in which information is being received by laser light (at least during transmission of the transmission information by laser light from the opposing device), then a change occurs in the relative position of the device itself and the opposing device. If the amount of this change in relative position is large then there is a possibility of laser light leakage from the space interposed between the device itself and the opposing device. The separation distance to the opposing device changes when the relative position of the device itself and the opposing device changes, and if the amount of change in the relative position is large then the amount of change in the separation distance also becomes large.

In the first aspect of the present invention, based on the above, a separation distance detection unit is provided for detecting or estimating whether or not there has been a change in the separation distance to the opposing device of a threshold value or above, the first control unit issues a warning, or halts emission of the laser light from the opposing device, if the separation distance detection unit detects or estimates that the separation distance to the opposing device has changed by a threshold value or above. Thereby, when the first control unit is configured so as to issue a warning when the separation distance detection unit detects or estimates that the separation distance to the opposing device has changed by a threshold value or above, if there is a comparatively large change in the relative position of the device itself and the opposing device, and a possibility arises of laser light leakage from the space interposed between the device itself and the opposing device, then the fact that there has been a change in the separation distance to the opposing device of a threshold value or above is detected or estimated by the separation distance detection unit. By issuing the warning, a user can be made aware that a state has arisen with a possibility of laser light leakage from the space interposed between the device itself and the opposing device, and the user can adopt counter measures to secure safety.

When the first control unit is configured so as to halt emission of the laser light from the opposing device when the separation distance detection unit has detected or estimated that there has been a change in the separation distance to the opposing device of the threshold value or above, if there is a comparatively large change in the relative position of the device itself and the opposing device and the possibility arises of laser light leakage from the space interposed between the device itself and the opposing device, then the fact that there has been a change in the separation distance to the opposing device of a threshold value or above is detected or estimated by the separation distance detection unit, and emission of the laser light from the opposing device is halted. Laser light leakage from the space interposed between the device itself and the opposing device can thereby be prevented before it occurs. Consequently, the first aspect of the present invention enables safety to be secured when the relative position to the opposing device has changed during transmission of information to the opposing device using laser light.

An electronic device according to a second aspect of the present invention includes: a first emission unit for emitting laser light; a first modulating unit for modulating the laser light emitted from the first emission unit according to transmission information, wherein the laser light emitted from the first emission unit is detected by a receiving device of an opposing device, and the transmission information is received by demodulation of the transmission information from the detection result of the laser light; a separation distance detection unit, determining whether or not there has been a change in the separation distance to the opposing device of a threshold value or above; and a second control unit, issuing a warning and/or halting emission of the laser light from the opposing device when determination is made by the separation distance detection unit that the separation distance to the opposing device has changed by a threshold value or above.

In the second aspect of the present invention, the device itself is provided with functionality to emit laser light modulated according to the transmission information. When the relative position of the casing of the opposing device and the casing of the device itself is in the adjusted state to the communication enabled position, with the laser light emitted from the device itself incident within the light receiving region provided on an external face of the casing of the opposing device, the transmission information is received by detecting the laser light incident within the light receiving region with the receiving device of the opposing device, and by demodulating the transmission information from the laser light detection result. In the invention of the second aspect of the present invention, the separation distance detection unit is also provided for detecting or estimating whether or not the separation distance to the opposing device has changed by the threshold value or above. The second control unit issues a warning or halts emission of the laser light from the first emission unit of the device itself if it is detected or estimated by the separation distance detection unit that the separation distance to the opposing device has changed by the threshold value or above.

Thereby, when the second control unit issues a warning if the separation distance detection unit detects or estimates that the separation distance to the opposing device has changed by the threshold value or above, this occurs when there is a comparatively large change in the relative position of the device itself and the opposing device. When a possibility arises that laser light leakage occurs from the space interposed between the device itself and the opposing device, the separation distance detection unit detects or estimates that the separation distance to the opposing device has changed by the threshold value or above, and a warning is issued. A user can thereby be made aware that a state has arisen with a possibility of laser light leakage from the space interposed between the device itself and the opposing device, and the user can adopt counter measures to secure safety.

Also, when the second control unit halts emission of the laser light from the device itself, and when the separation distance detection unit detects or estimates that the separation distance to the opposing device has changed by the threshold value or above, there is a comparatively large change in the relative position of the device itself and the opposing device. As a result, when a possibility arises of laser light leakage occurring from the space interposed between the device itself and the opposing device, the separation distance detection unit detects or estimates that the separation distance to the opposing device has changed by the threshold value or above, and the emission of the laser light from the device itself is halted. Thereby laser light leakage from the space interposed between the device itself and the opposing device can thereby be prevented before it occurs. This consequently enables safety to be secured, in a similar manner to in the first aspect of the present invention, when the relative position to the opposing device has changed during transmission of information to the opposing device using laser light.

When a wireless communication unit for carrying out wireless communication with the opposing device using electromagnetic waves other than laser light is provide in the first or second aspects of the present invention, the separation distance sensor unit can be configured so as to estimate whether or not the separation distance to the opposing device has changed by the threshold value or above by use of the wireless communication unit. Specifically, configuration may be made such that estimation as to whether or not during wireless communication with the opposing device by the wireless communication unit the separation distance to the opposing device has changed by the threshold value or above is made based on the intensity of the electromagnetic field from the opposing device detected by the wireless communication unit, and/or based on an error rate detected in wireless communication by the wireless communication unit.

The first aspect and the second aspect of the present invention may be configured: with the separation distance detection unit provided with a detection section for detecting light emitted from a light emitting section and reflected by the casing of the opposing device, and/or an electric field or a magnetic field generated by an electromagnetic field generating section provided to the casing of the opposing device; and with detection of whether or not the separation distance to the opposing device has changed by the threshold value or above being based on detection by the detection section of the amount of reflected light, the irradiation position of the reflected light, the strength of the electric field, and/or the strength of the magnetic field.

The first aspect and the second aspect of the present invention may also be configured: with the separation distance detection unit including a moveable member provided so as to contact the casing of the opposing device and to displace when the relative position of the casing of the opposing device and a casing of the device itself is in an adjusted state to a position enabling communication, and a displacement detection section for detecting displacement of the moveable member; and with detection of whether or not the separation distance to the opposing device has changed by the threshold value or above being based on the detected state of displacement of the moveable member by the displacement detection section.

The first aspect of the present invention may also be configured, when provided with a first transmission unit capable of transmitting information to the opposing device (this first transmission unit may be configured to transmit information by laser light, or may be configured to transmit information by electromagnetic waves other than laser light), so that the first control unit halts emission of the laser light from the opposing device by transmitting instruction information to the opposing device, instructing halting of laser light emission, using the first transmission unit.

The first aspect of the present invention may also be configured to include a second transmission unit for periodically transmitting specific information to the opposing device during period(s) when the receiving device is receiving transmission information normally from the opposing device (this second transmission unit may also be configured to transmit information by laser light, or may be configured to transmit information by electromagnetic waves other than laser light). When the opposing device is configured to emit laser light modulated according to the transmission information from the first emission unit during the period in which the specific information is being periodically received, the first control unit halts emission of the laser light from the opposing device by halting transmission of the specific information to the opposing device by the second transmission unit.

The electronic device according to the first aspect of the present invention may also be configured to further include a second emission unit for emitting laser light and a second modulating unit for modulating the laser light emitted from the second emission unit according to transmission information. When configured for carrying out two-way communication with the opposing device by laser light, configuration is preferably made such that emission of the laser light from the second emission unit is also halted when the first control unit halts emission of the laser light from the opposing device.

In the second aspect of the present invention, the opposing device is configured to further include a second emission unit for emitting laser light and a second modulating unit for modulating the laser light emitted from the second emission unit according to transmission information, and the opposing device is configured for carrying out two-way communication with the device itself by laser light. When the second control unit halts emission of the laser light from the first emission unit of the device itself, configuration is preferably made such that emission of the laser light from the second emission unit of the opposing device is also halted by transmitting to the opposing device as the transmission information instruction, information instructing halting of the emission of the laser light from the second emission unit, or by transmitting the instruction information by a third transmission unit capable of transmitting information to the opposing device (a configuration for transmitting information by electromagnetic waves other than laser light may be applied to this third transmission unit).

Laser light of any wavelength may be applied to the laser light in the first aspect and the second aspect, however preferable laser light for the present invention is non-visible laser light with a wavelength outside of the visible region, which cannot be visually confirmed. Laser light with a wavelength in the infrared region is particularly preferable for the non-visible laser light, from the perspective of high speed communication realization.

The electronic device according to the first and the second aspects of the present invention may be any device capable of carrying out transmission of information by laser light, and application can be made, for example, to an imaging device, a portable information device, a transportable radiographic imaging conversion device, or an image read-out device for reading out image information from such a transportable radiographic imaging conversion device.

As explained above, the present invention exhibits the excellent effect of enabling safety to be secured when the relative position to an opposing device has changed during transmission of information to the opposing device using laser light. This is accomplished by provision of a separation distance detection unit for detecting or estimating whether or not the separation distance, to the opposing device receiving information by laser light, has changed by the threshold value or above, and by issuing a warning or halting emission of the laser light when the separation distance detection unit detects or estimates that the separation distance to the opposing device has changed by the threshold value or above.

3C is a perspective view showing the respective dispositions of an electronic cassette and of an image reading device during image readout from the electronic cassette.

Figure 4A:
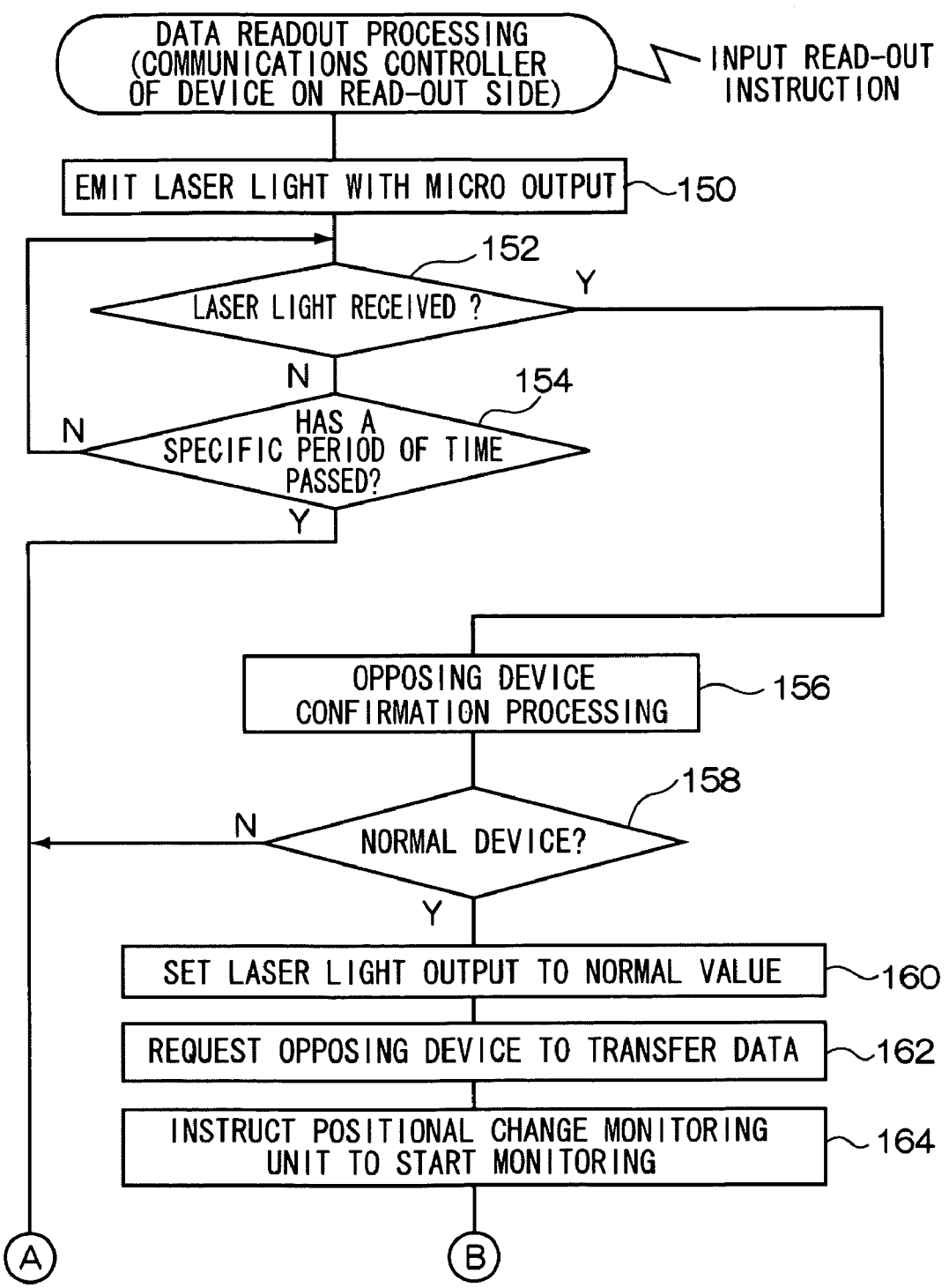
Figure 4B:
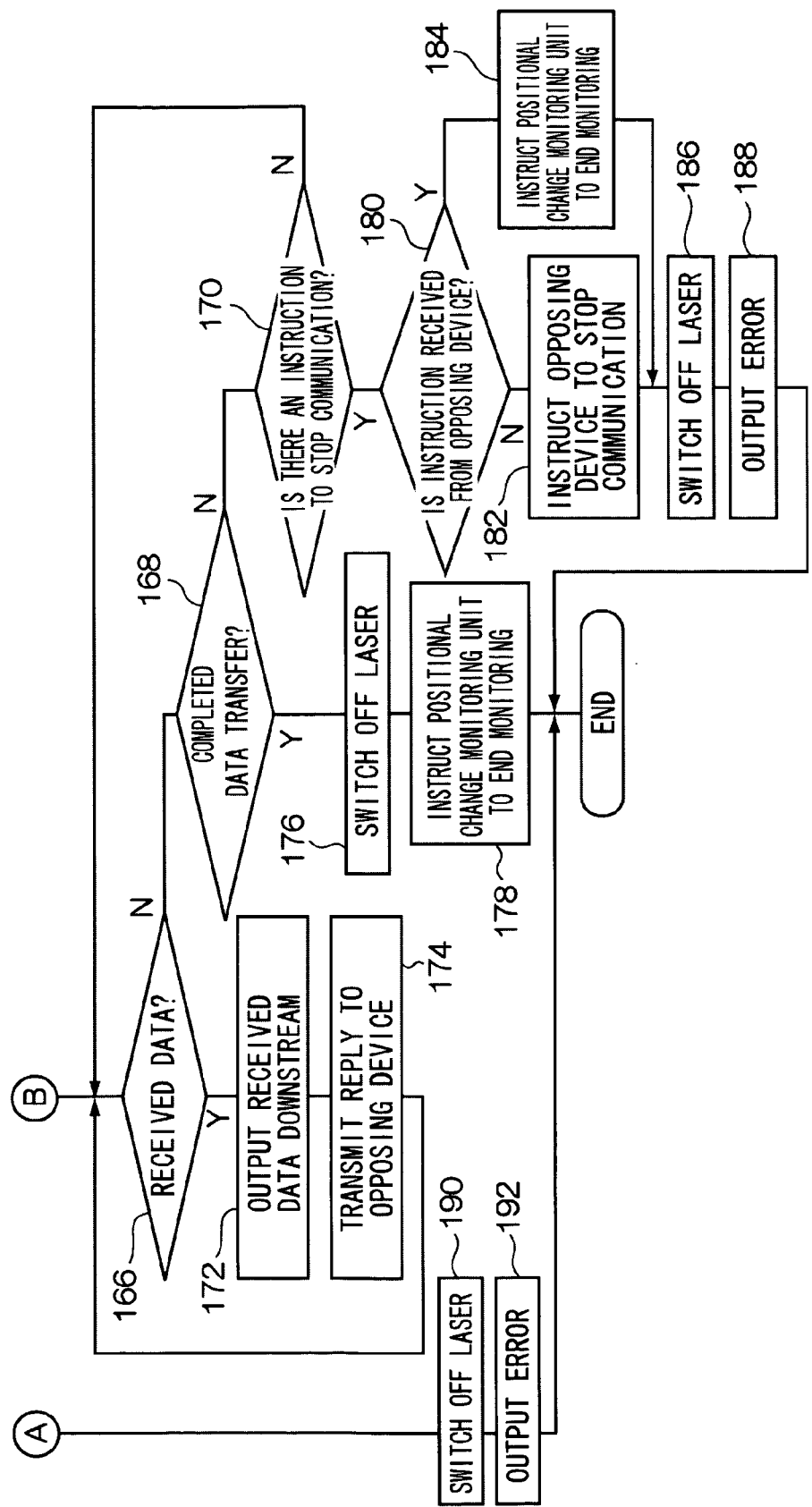

FIG. 4A and FIG. 4B are flow charts showing the contents of data readout processing.

Figure 5A:
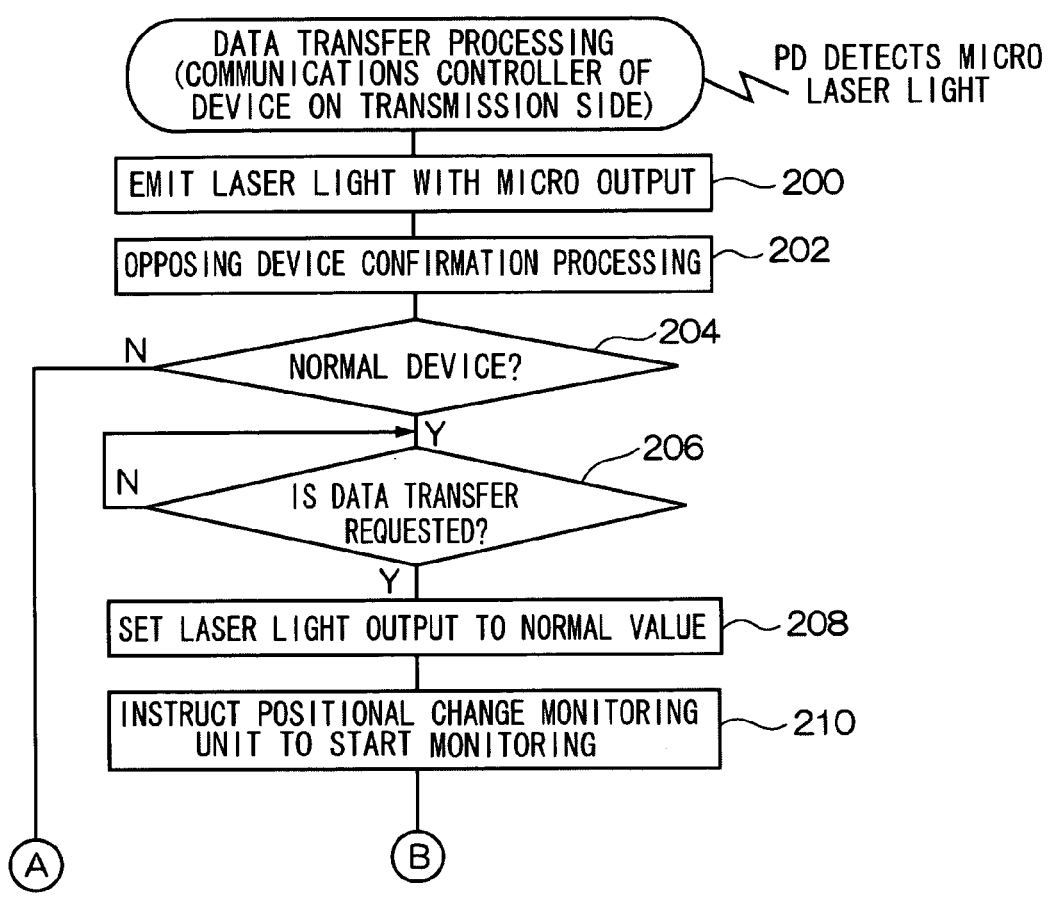
Figure 5B:
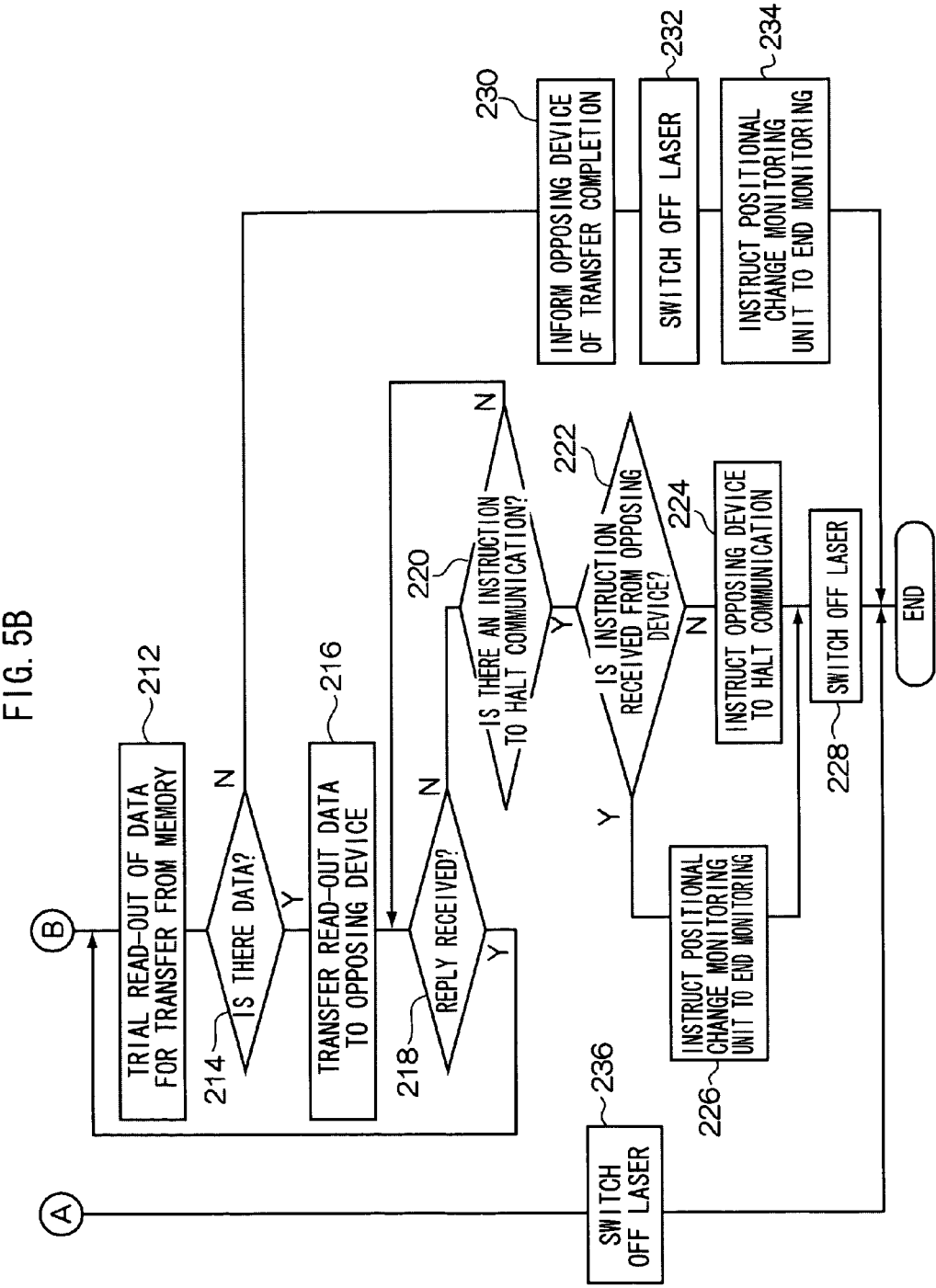

FIG. 5A and FIG. 5B are flow charts showing the contents of data transfer processing.

Figure 6A:
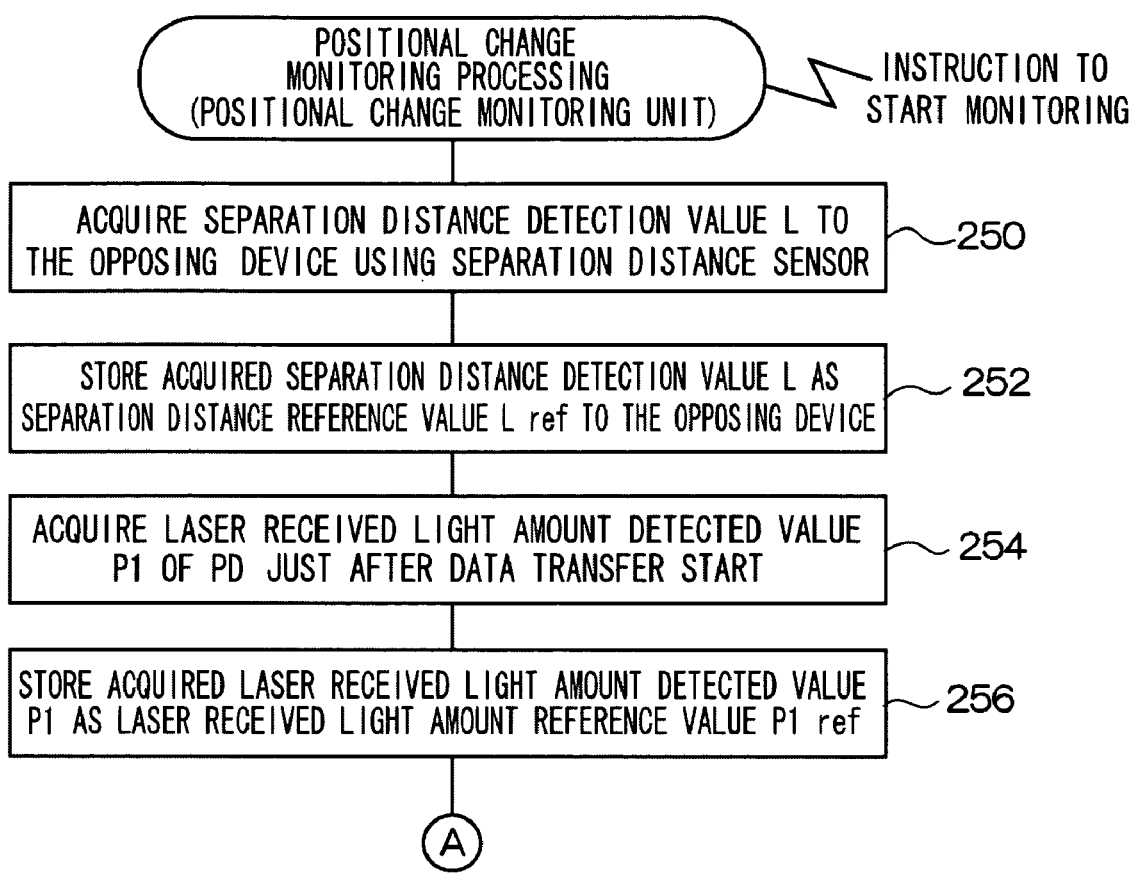
Figure 6B:
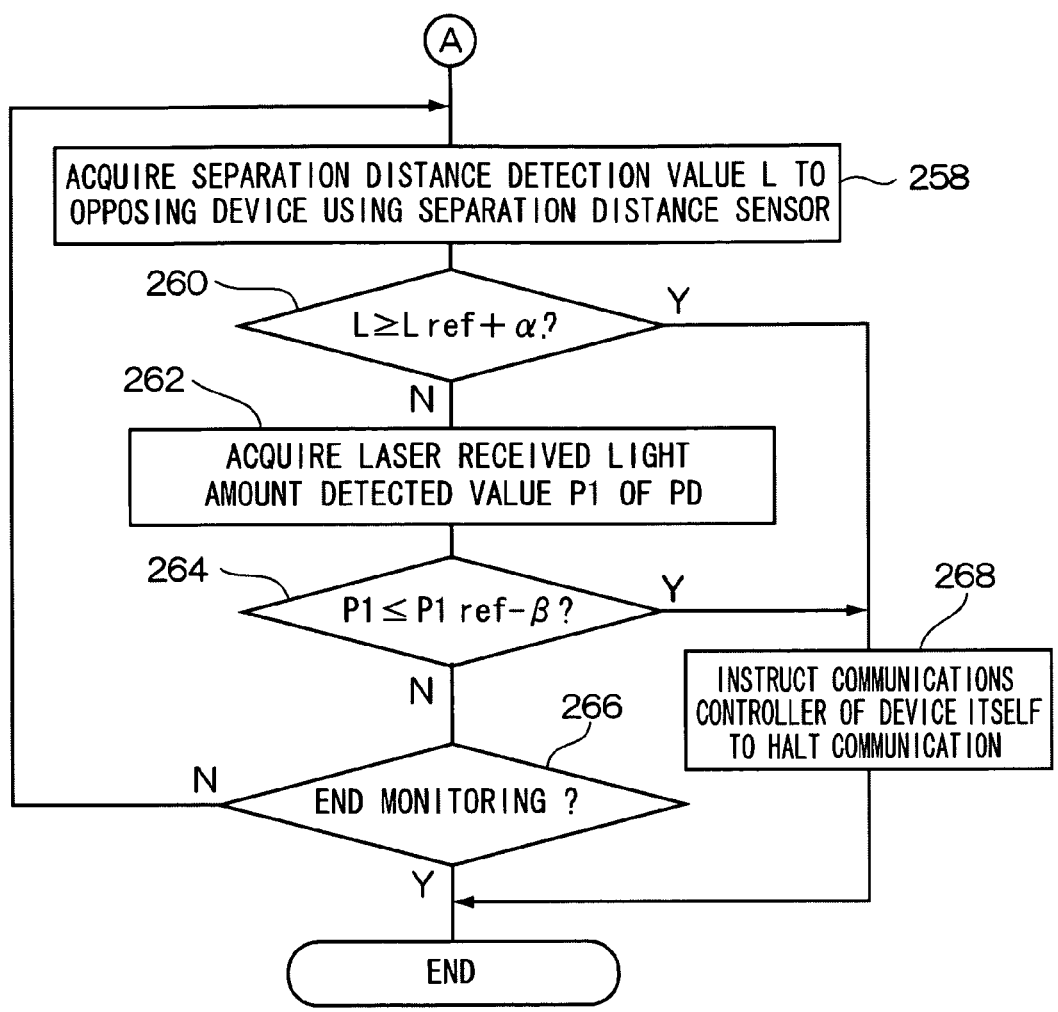

FIG. 6A and FIG. 6B are flow charts showing the contents of positional change monitoring processing according to the first exemplary embodiment.

FIG. 7A and FIG. 7B are schematic diagrams for explaining detection of positional change based on a distance detection value.

Figure 8A:
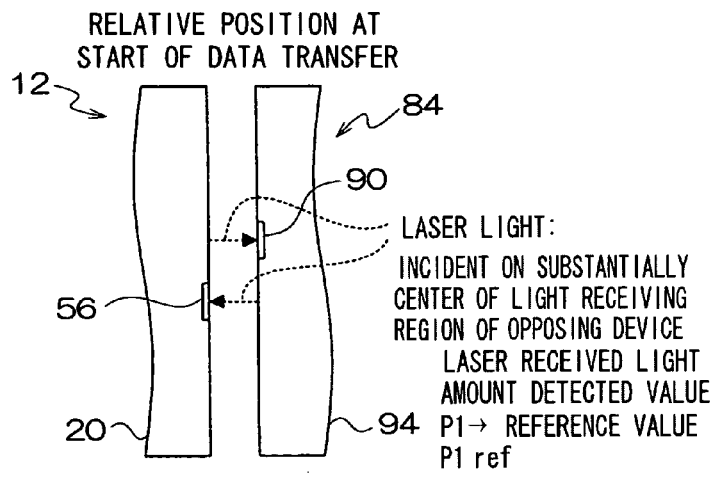
Figure 8B:
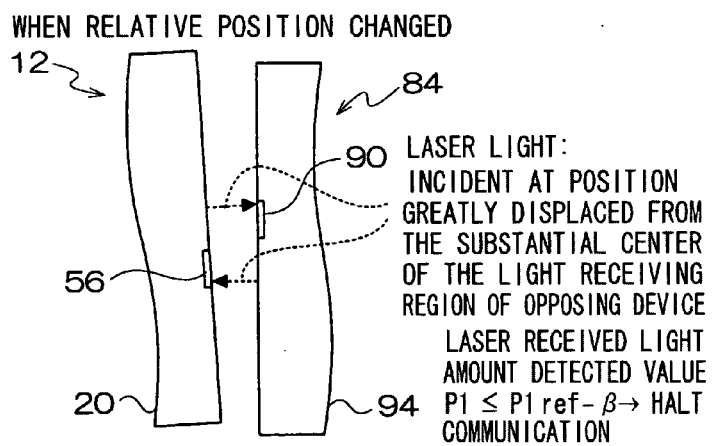
Figure 8C:
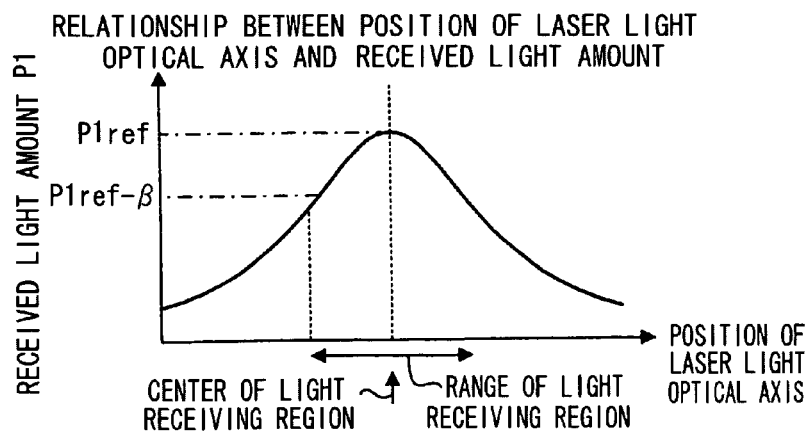

FIG. 8A, FIGS. 8B and 8C are schematic diagrams for explaining detection of positional change based on received laser light amount.

FIG. 9 is a block diagram showing, according to a second exemplary embodiment, a schematic configuration of an electronic cassette and an image reading device.

Figure 10A:
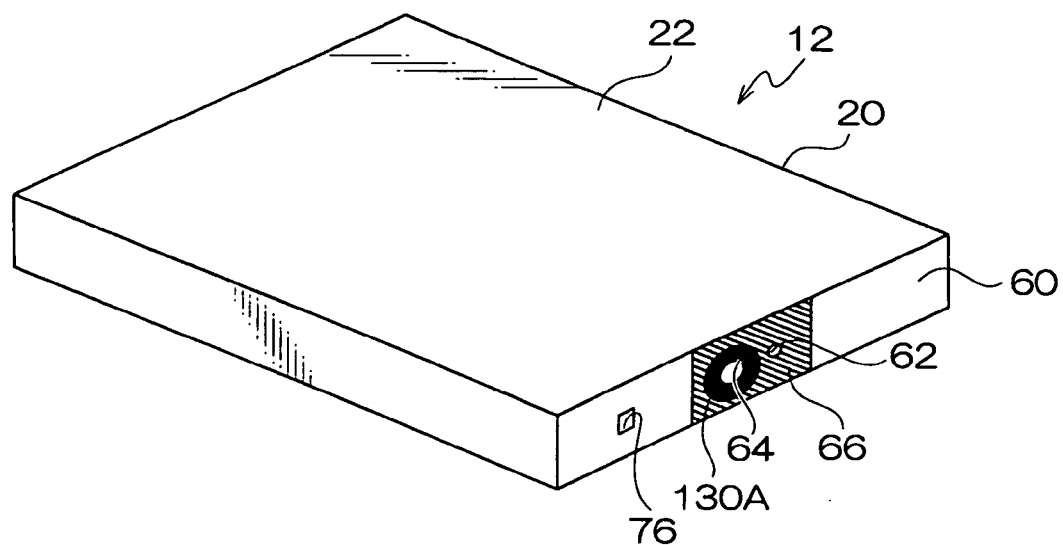
Figure 10B:
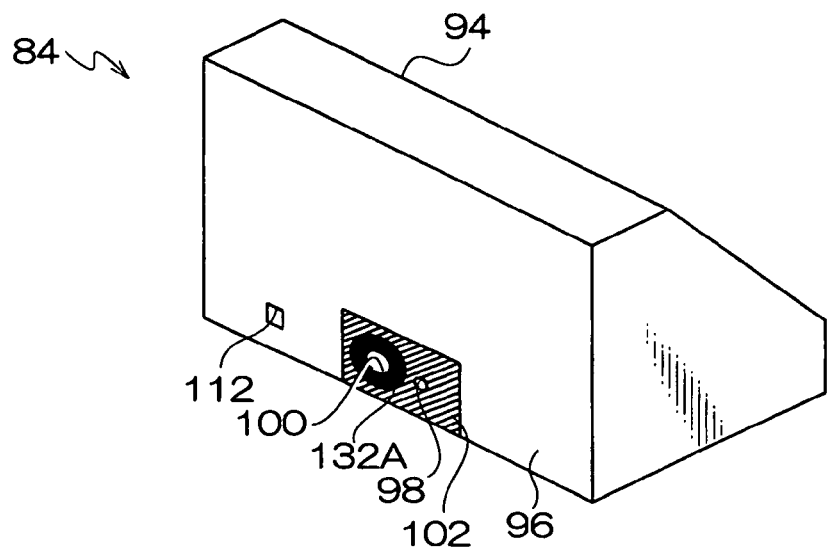

FIG. 10A and FIG. 10B are perspective views showing, according to the second exemplary embodiment, respective external views of an electronic cassette and an image reading device.

Figure 11A:
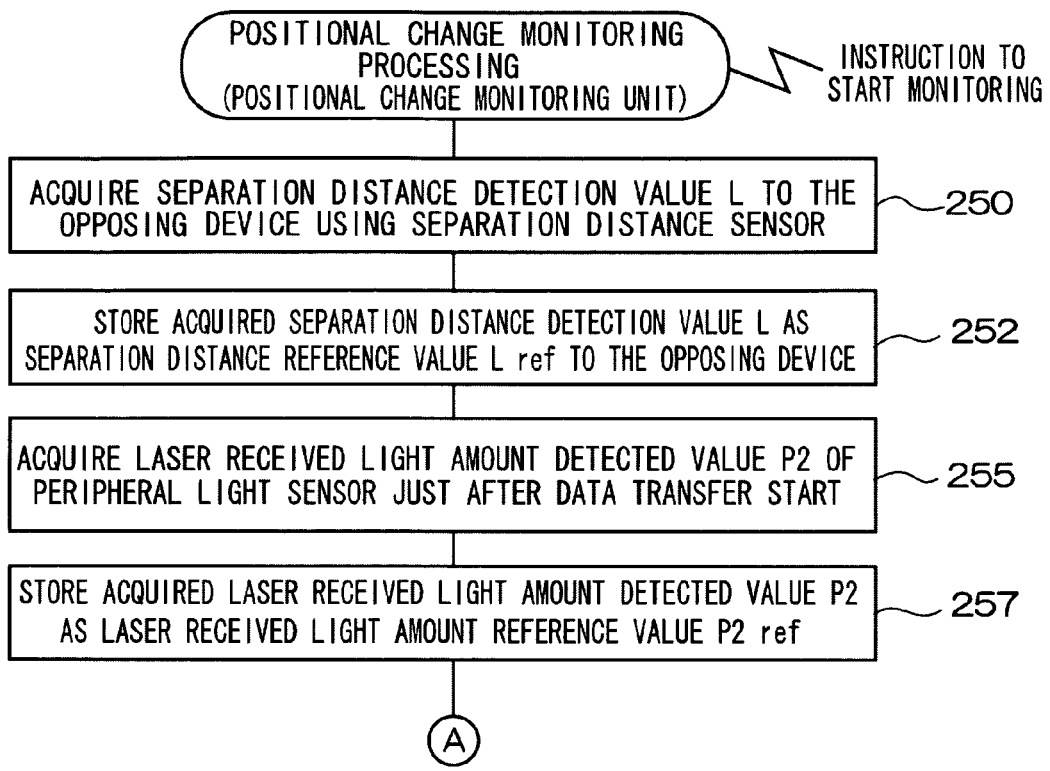
Figure 11B:
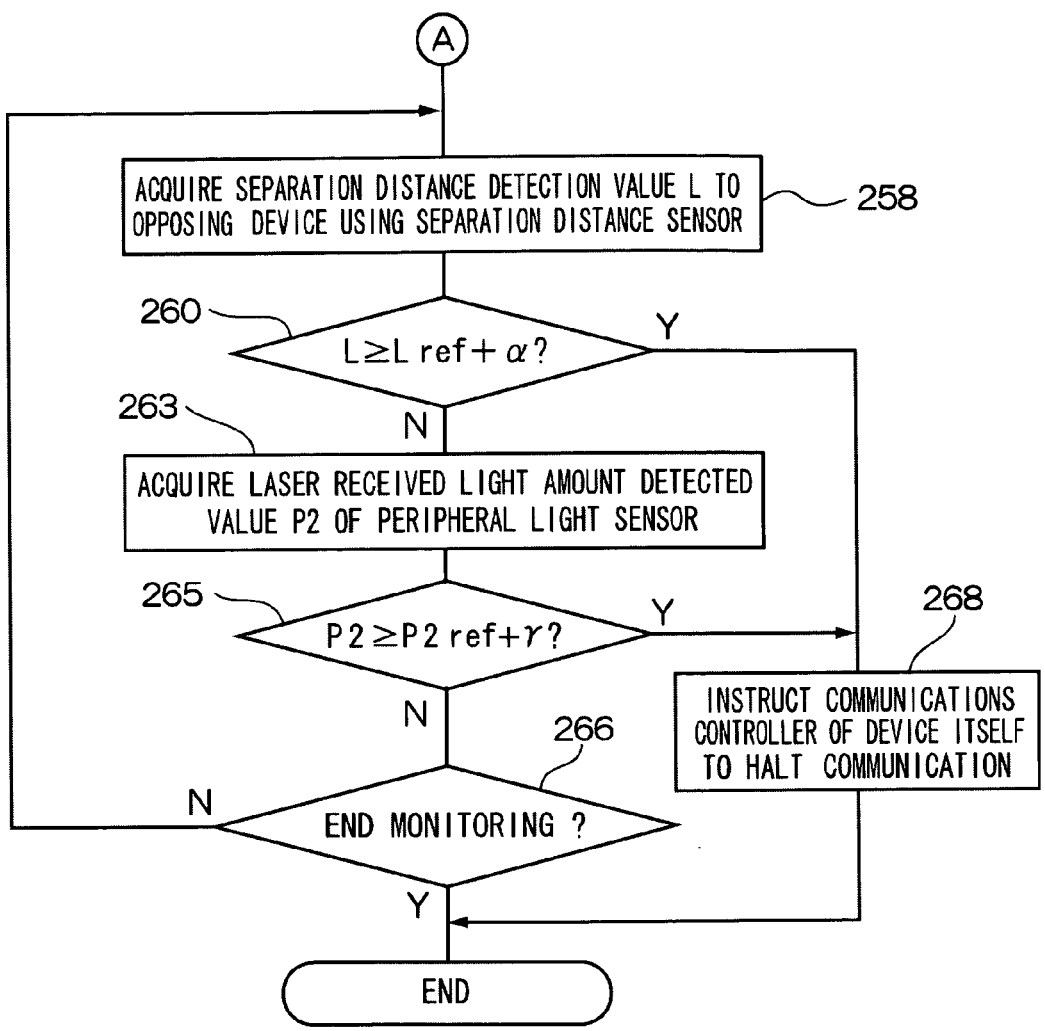

FIG. 11A and FIG. 11B are flow charts showing the contents of positional change monitoring processing according to the second exemplary embodiment.

FIG. 12A, FIGS. 12B and 12C are schematic diagrams for explaining detection of positional change based on received light amount of a peripheral light sensor.

DETAILED DESCRIPTION OF THE INVENTION

Explanation will now be given of details of exemplary embodiments of the present invention, with reference to the drawings.

First Exemplary Embodiment

Figure 1:
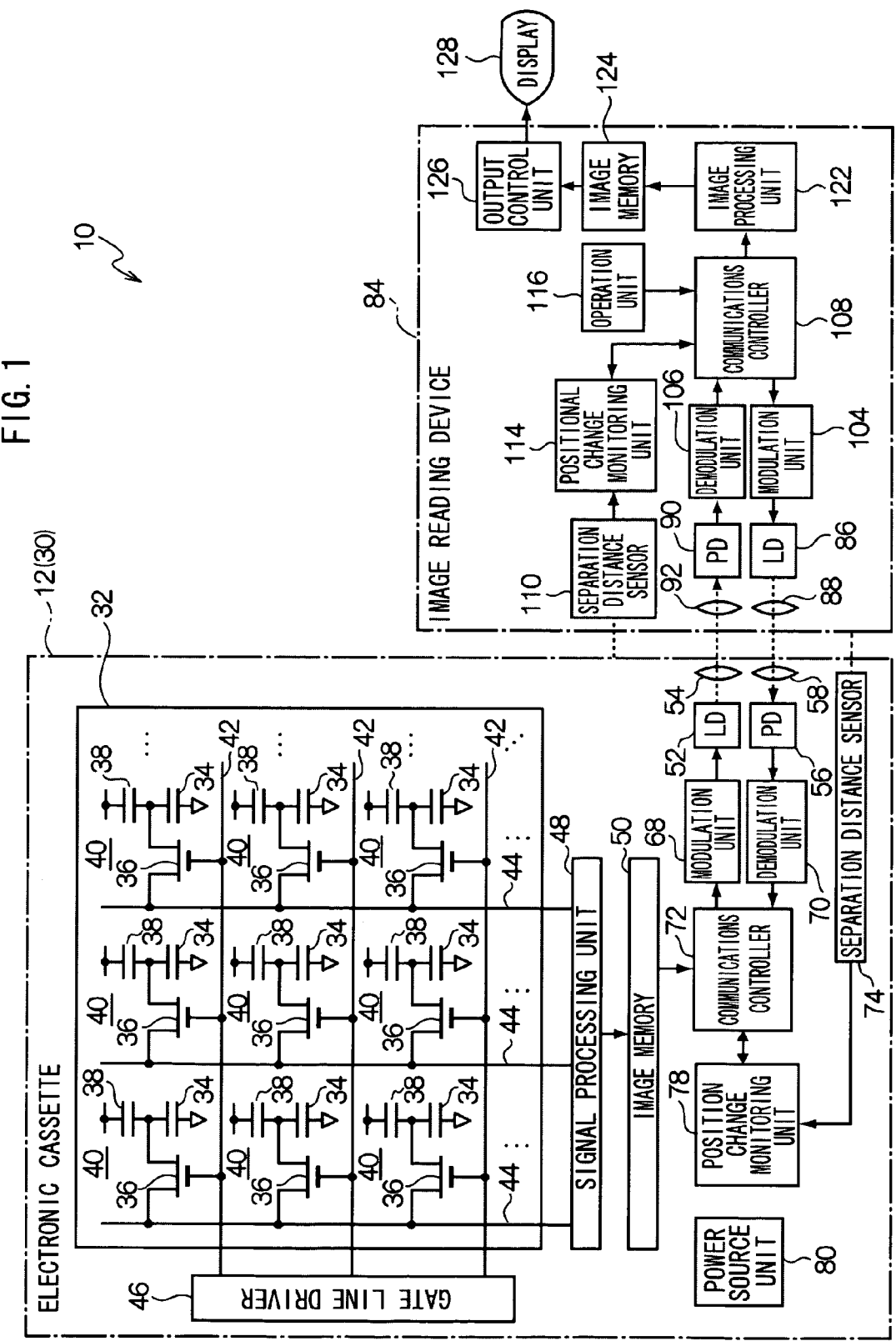
FIG. 1 is a block diagram showing, according to a first exemplary embodiment, a schematic configuration of an electronic cassette and an image reading device.

A radiographic imaging handling system 10 according to the present exemplary embodiment is shown in FIG. 1. The radiographic imaging handling system 10 is configured to include a portable electronic cassette 12, the electronic cassette 12 being capable of converting into image data and storing the image information carried by radiation each time the electronic cassette 12 is irradiated, and to include an image reading device 84 capable of reading out image data stored in the electronic cassette 12. It should be noted that each of the electronic cassette 12 and the image reading device 84 correspond to the electronic device of the present invention. The electronic cassette 12 also corresponds to the portable radiographic image conversion device of the present invention, and the image reading device 84 also corresponds to the image reading device of the present invention.

Figure 2A:
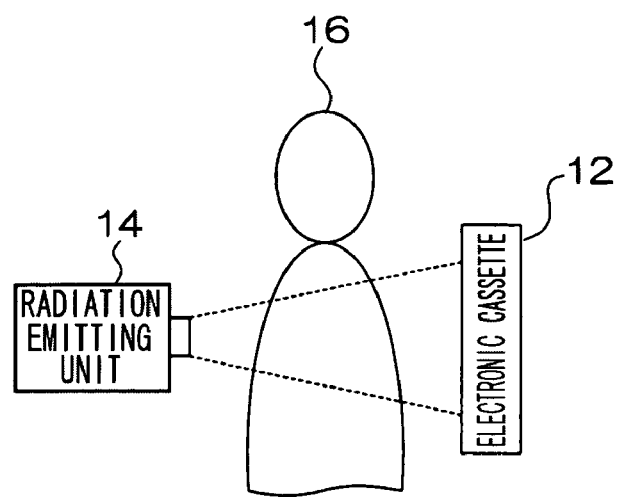
FIG. 2A is a schematic diagram the disposition of an electronic cassette during radiographic imaging.

During imaging of a radiographic image the electronic cassette 12 is disposed with a separation between the electronic cassette 12 and a radiation emitting unit 14 that generates radiation, such as X-rays or the like, as shown in FIG. 2A. An imaging subject 16 is positioned at an imaging position between the radiation emitting unit 14 and the electronic cassette 12, and when the taking of a radiographic image is instructed the radiation emitting unit 14 emits radiation of a radiation amount in accordance with preset imaging conditions or the like. The radiation radiated from the radiation emitting unit 14 picks up image information by transmission through the imaging subject 16 positioned at the imaging position, and is then irradiated onto the electronic cassette 12.

Figure 2B:
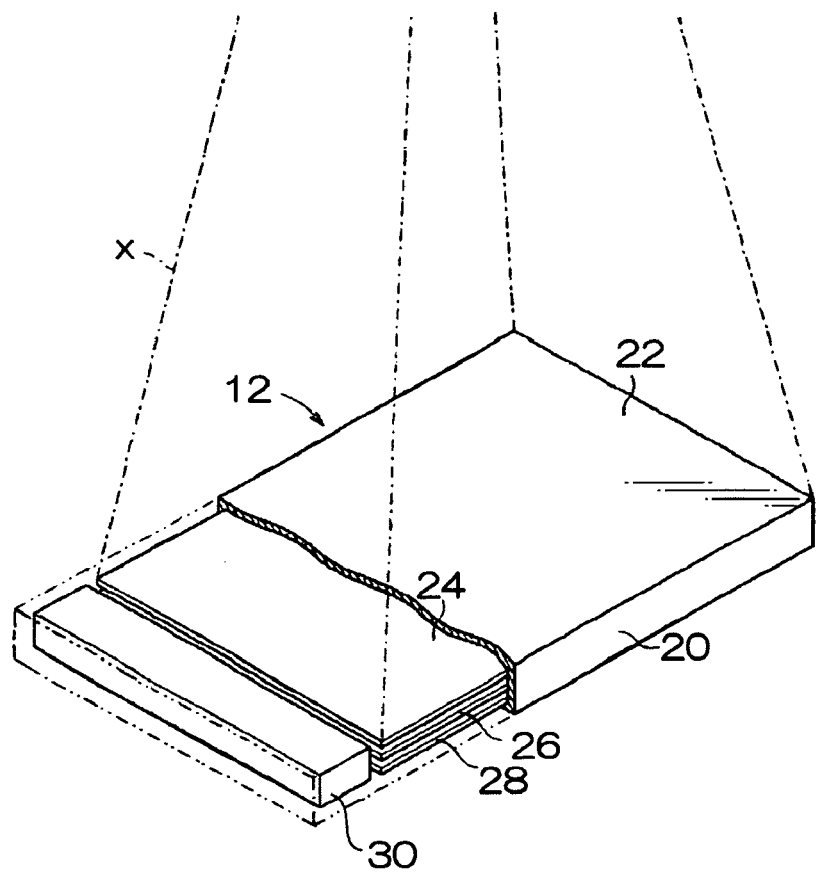
FIG. 2B is a perspective diagram showing the internal structure of an electronic cassette.

The electronic cassette 12 is covered by a flat plate-shaped casing 20 formed of a thickness of material such that X-rays can be transmitted therethrough, as shown in FIG. 2B. Within the casing 20 are disposed, in sequence from an irradiation face 22 of the casing 20, onto which the X-rays are irradiated, a grid 24 for removing any scattered X-rays generated due to transmission through the imaging subject 16, a radiation detector (radiation detection panel) 26 for detecting X-rays, and a lead plate 28 for absorbing back-scattering X-rays. It should be noted that the irradiation face 22 of the casing 20 may be configured by the grid 24. In addition a case 30 for accommodating a microcomputer containing various circuits (described later) is disposed at one end within the casing 20. It is also preferable to dispose a lead plate or the like at the irradiation face 22 side of the case 30 in order to avoid the various circuits within the case 30 being damaged during irradiation with X-rays.

The radiation detector 26 of the electronic cassette 12 is configured with a TFT active matrix board 32, as shown in FIG. 1, layered thereon with a photoelectric conversion layer for absorbing X-rays and converting them into charge. The photoelectric conversion layer is formed with, for example, selenium as a main component thereof (for example contained at a proportion of 50% or above) using non-crystalline a-Se (amorphous selenium). When radiation is irradiated onto the photoelectric conversion layer, the photoelectric conversion layer converts irradiated radiation into charge by generating a charge (electron-hole pair) within the layer of an amount of electric charge in accordance with the irradiated radiation. Disposed in a matrix shape on the TFT active matrix board 32 are plural individual pixel portions 40. Each of the pixel portions 40 is provided with an individual storage capacitor 34 for accumulating charge generated in the photoelectric conversion layer, and a TFT 36 for reading out the charge accumulated in the storage capacitor 34 (in FIG. 1 the photoelectric conversion layer corresponding to each of the individual pixel portions 40 is shown pictorially as photoelectric conversion portions 38). The charge generated in the photoelectric conversion layer, by irradiation of the electronic cassette 12 with radiation, is accumulated in the respective storage capacitor 34 of the individual pixel portions 40. In this manner, the image-information-carrying radiation that is irradiated onto the electronic cassette 12 is converted into charge information, and held in the radiation detector 26.

The TFT active matrix board 32 is provided with plural gate lines 42 extending along a fixed direction (row direction) for switching on and off the TFT 36 of the individual pixel portions 40, and is provided with plural data lines 44 extending in a direction perpendicular to the gate lines 42 (column direction) for reading out accumulated charge from the storage capacitors 34 through the TFTs 36 that are switched on. Individual gate lines 42 are connected to a gate line driver 46, and individual data lines 44 are connected to a signal processing unit 48. When charge has been accumulated in the storage capacitor 34 of individual pixel portions 40, the TFTs 36 of the individual pixels 40 are switched on in sequence of single row units by a signal supplied from the gate line driver 46 through the gate lines 42, and the charge that has been accumulated in the storage capacitor 34 of the pixel portions 40 for which the TFT 36 is on, is transmitted as a charge signal through the data lines 44 and input to the signal processing unit 48. The charge that has been accumulated in the storage capacitors 34 of individual pixel portions 40 is consequently read out in sequence in single row units.

While not illustrated in the figures, the signal processing unit 48 is provided with a amplifier and a sample and hold circuit for each of the individual data lines 44. After the charge signal transmitted through the data line 44 has been amplified by the amplifier it is then held in the sample and hold circuit. An A/D convertor is connected in sequence to the output side of the sample and hold circuits, and the charge signals held in the individual sample and hold circuits are input in sequence (serially) into a multiplexer, and converted into digital image data by the A/D convertor. There is an image memory 50 connected to the signal processing unit 48, and image data output from the A/D convertor of the signal processing unit 48 is stored in sequence in the image memory 50. The image memory 50 has a capacity capable of storing image data equivalent to plural films, and each time radiographic imaging is carried out the image data obtained by imaging is stored in sequence in the image memory 50.

Figure 3A:
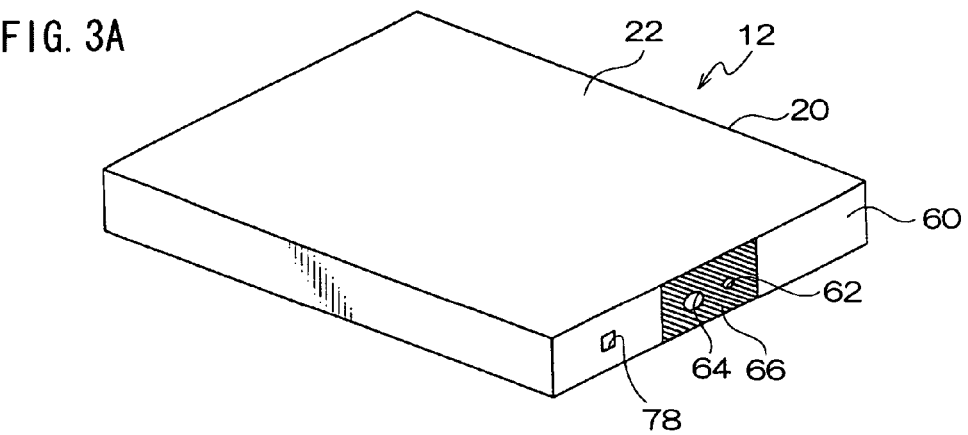
FIG. 3A is an external view of an electronic cassette.

The electronic cassette 12 also has functionality for wireless communication using laser light with the image reading device 84, and is provided with a LD (Laser Diode) 52 as laser light source, and a PD (Photo Diode) 56 for detecting incident laser light from outside. In order to give high speed communication between the electronic cassette 12 and the image reading device 84 the LD 52 is preferably an LD emitting laser light with a wavelength in the infrared region, and the PD 56 is preferably a PD sensitive to wavelengths in the infrared region. In the present exemplary embodiment, as shown in FIG. 3A, there is an emission hole 62 and a light receiving hole 64, each provided in a specific side face 60 of the casing 20 of the electronic cassette 12 (this face is disposed so as to face the casing of the image reading device 84 during communication with the image reading device 84, and is referred to below as "opposing face 60"). The emission hole 62 is for letting laser light emitted from the LD 52 pass through, and the light receiving hole 64 is for letting laser light from outside pass through (for example from the image reading device 84). It should be noted that while in FIG. 3A the opposing face 60 provided with the emission hole 62 and the light receiving hole 64 is a side face that contacts a short side of the irradiation face 22 there is no limitation thereto, and the opposing face 60 may be a side face that contacts a long side of the irradiation face 22, may be the bottom face (the face on the opposite side to the irradiation face 22) etc.

The laser light emitted from the LD 52 is transmitted through a lens 54 disposed on the laser light emission side of the LD 52 (see FIG. 1), passes through the emission hole 62 and is emitted out from the casing 20. Laser light from outside passes through the light receiving hole 64, is transmitted through a lens 58 disposed on the incident light side of the PD 56 (see FIG. 1), and is received as light by the PD 56. A portion of the region of the opposing face 60 of the casing 20 of the electronic cassette 12, including the periphery of the light receiving hole 64 (and of the emission hole 62), is covered by a diffusing material 66 capable of diffusing reflected light of the irradiated laser light by variously reflecting the irradiated laser light in multiple mutually different directions.

As the diffusing material 66, for example, the surface can be applied with a member of which surface is profiled such that, within miniature regions of surface area of that of the irradiated region when laser light (described later) is emitted from the image reading device 84 or smaller surface area, there are plural portions present which each have mutually different reflection directions to irradiated light. Reflected light from an irradiated laser light can thereby be diffused with certainty. Most preferable for the diffusing material 66 is a member of which surface is profiled such that there are uniformly distributed semi-spherical shaped protrusion portions on the surface of a size $\frac{1}{10}$ the wavelength of the laser light irradiated or smaller. The dependency on incident angle can be reduced by forming the individual semi-spherical shaped protrusion portions in the above manner, and by making the individual protrusion portions of a size $\frac{1}{10}$ the wavelength of the laser light irradiated or smaller, Rayleigh scattering occurs and even more pronounced diffusion of the irradiated laser light can be achieved.

The LD 52 is connected to a communications controller 72 through a modulation unit 68. The communications controller 72 is realized by a microcomputer, and when information is being transmitted to the image reading device 84, the communications controller 72 outputs transmission information to the modulation unit 68, and also instructs the modulation unit 68 to modulate the intensity of the laser light for emission from the LD 52. The modulation unit 68 modulates the laser light emitted from the LD 52 according to the transmission information that has been input with a specific modulation formula, and the modulation unit 68 controls driving of the LD 52 such that the intensity of the laser light emitted from the LD 52 matches the instructed intensity. The laser light modulated according to the transmission information is thereby emitted from the LD 52 at the intensity instructed by the communications controller 72.

The PD 56 is connected to the communications controller 72 through a demodulation unit 70. Laser light from outside is received by the PD 56, and when a received light amount signal according to the received light amount of the laser light is input to the demodulation unit 70 from the PD 56, the demodulation unit 70, based on the input received light amount signal, demodulates the information carried on the received light of the laser light with a specific demodulation formula (the information sent from the opposing device in the communication). The demodulated information is output by the demodulation unit 70 to the communications controller 72 and at the same time the received light amount of the laser light using the PD 56 is detected, and the detection result of the laser light received light amount is also output to the communications controller 72. The communications controller 72 carries out later described data transfer processing (FIG. 5A and FIG. 5B).

There is a separation distance sensor 74 provided to the electronic cassette 12. In the present exemplary embodiment the separation distance sensor 74 is provided with a light emitting element and a photo receptor element, and uses a configuration in which the duration of time is measured from when light is emitted from the light emitting element until the emitted light has been reflected by the target object and received by the photoreceptor element, and the separation distance to the target object is detected based on the duration measured. A detection hole 76 is provided in the opposing face 60 of the casing 20 of the electronic cassette 12, as shown in FIG. 3A, and light emitted from the light emitting element of the separation distance sensor 74 passes through the detection hole 76 and is irradiated on the target object present in front of the opposing face 60. Light reflected by the target object passes through the detection hole 76 and is received by the photoreceptor element. The separation distance sensor 74 corresponds to the distance detection unit of the present invention.

The communications controller 72 and the separation distance sensor 74 are connected to a position change monitoring unit 78. The position change monitoring unit 78 is also realized by a microcomputer. Detailed explanation will be given later, but in general terms, when the device itself (the electronic cassette 12) is communicating with the image reading device 84, the position change monitoring unit 78 carries out positional change monitoring processing (see FIG. 6A and FIG. 6B) for monitoring any change in the relative position between the device itself (the electronic cassette 12) and the image reading device 84. The position change monitoring unit 78 does this by monitoring the received light amount of the laser light detected by the demodulation unit 70 and monitoring any change in the separation distance detected by the separation distance sensor 74.

There is a power source unit 80 provided to the electronic cassette 12, and the various circuits and various elements described above (the gate line driver 46, the signal processing unit 48, the image memory 50, microcomputer(s) with the functionality of the communications controller 72, and the position change monitoring unit 78, the modulation unit 68, the LD 52, the PD 56, the demodulation unit 70, the separation distance sensor 74 etc.) are driven by power supplied from the power source unit 80. Configuration of the power source unit 80 is preferably by an internal battery (a rechargeable battery) so that the portability of the electronic cassette 12 is not compromised, with supply of power to the various circuits and elements from a charged battery. However disposable batteries may be used as the battery, or a configuration may be made with constant connection to a commercial power source, with rectification and voltage transformation of the power supplied from the commercial power source before supplying power to the various circuits and elements.

Figure 3B:
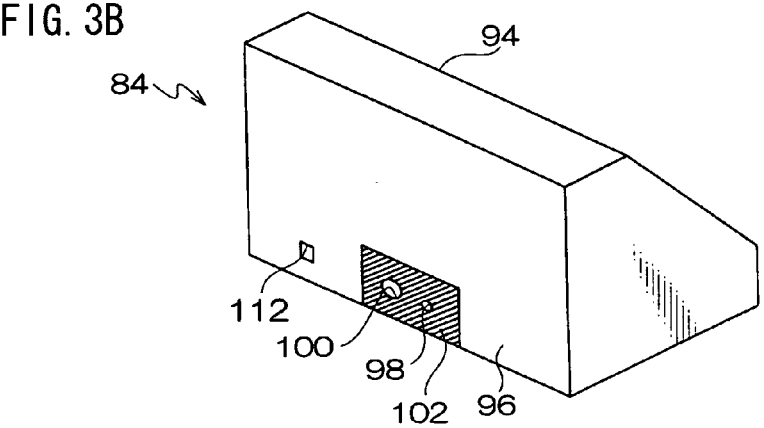
FIG. 3B is an external view of an image reading device, and FIG.

The image reading device 84 also has functionality to carry out wireless communication by laser light with the electronic cassette 12 and is provided with a LD 86 as laser light source and with a PD 90 for detecting incident laser light from outside. In order to achieve high speed communication between the electronic cassette 12 and the image reading device 84, in the same manner as with the electronic cassette 12, the LD 86 preferably is an LD emitting laser light of wavelength in the infrared region and the PD 90 is preferably a PD with sensitivity to a wavelength in the infrared region. In the present exemplary embodiment, as shown in FIG. 3B, there is a specific side face 96 of a casing 94 covering the exterior of the image reading device 84 (this side face is disposed so as to face the casing of the electronic cassette 12 during communication with the electronic cassette 12, this face is referred to as "opposing face 96" below). An emission hole 98 for letting laser light emitted from the LD 86 pass through, and a light receiving hole 100 for letting laser light from outside (for example from the electronic cassette 12) pass through, are each provided in the opposing face 96.

It should be noted that the emission hole 98 and the light receiving hole 100 provided in the opposing face 96 have respective separations and heights from the bottom face of the casing 94 equivalent to the separations and heights from the bottom face of the casing 20 of the emission hole 62 and the light receiving hole 64 provided in the opposing face 60. In a state in which the opposing face 60 of the electronic cassette 12 is facing and aligned with the casing 94 of the image reading device 84 (the state shown in FIG. 3C), the light receiving hole 100 is disposed so as to face the emission hole 62, and the emission hole 98 is disposed so as to face the light receiving hole 64.

The laser light emitted from the LD 86 passes through a lens 88 disposed at the laser light emission side of the LD 86 (see FIG. 1), and is emitted out from the casing 94 through the emission hole 98. Laser light from outside passes through the light receiving hole 100, passes through a lens 92 disposed on the on the incident light side of the PD 90 (see FIG. 1), and is received by the PD 90. A portion of the region of the opposing face 96 of the casing 94 of the image reading device 84 including the periphery of the light receiving hole 100 (and of the emission hole 98) is covered by a diffusing material 102 in a similar manner to with the electronic cassette 12.

The LD 86 is connected to a communications controller 108 through a modulation unit 104. The communications controller 108 is realized by a microcomputer, and when information is being transmitted to the electronic cassette 12, the communications controller 108 outputs transmission information to the modulation unit 104, and also instructs the modulation unit 104 to modulate the intensity of the laser light for emission from the LD 86. The modulation unit 104 modulates the laser light emitted from the LD 86 with a specific modulation formula according to the transmission information that has been input, and the modulation unit 104 controls driving of the LD 86 such that the intensity of the laser light emitted from the LD 86 matches the instructed intensity. Laser light modulated according to the transmission information is thereby emitted from the LD 86 at the intensity instructed by the communications controller 108.

The PD 90 is connected to the communications controller 108 through a demodulation unit 106. Light is received from outside by the PD 90, and when a received light amount signal according to the received light amount of the laser light is input to the demodulation unit 106 from the PD 90, the demodulation unit 106, based on the input received light amount signal, demodulates the information carried on the received laser light with a specific demodulation formula (the information sent from the opposing device in the communication). The demodulated information is output by the demodulation unit 106 to the communications controller 108 and at the same time the received light amount of the laser light using the PD 90 is detected, and the detection result of the laser light received light amount is also output to the communications controller 108. The communications controller 108 carries out later described data readout processing (FIG. 4A and FIG. 4B).

There is a separation distance sensor 110 provided to the image reading device 84. In the present exemplary embodiment the separation distance sensor 110 is provided with a light emitting element and a photo receptor element, in the same manner as the separation distance sensor 74 described above, and uses a configuration in which the separation distance to the target object is detected based on the duration of time from when light is emitted from the light emitting element until the emitted light has been reflected by the target object and received by the photoreceptor element. A detection hole 112 is provided in the opposing face 96 of the casing 94 of the image reading device 84, as shown in FIG. 3B, and light emitted from the light emitting element of the separation distance sensor 110 passes through the detection hole 112 and is irradiated on the target object present in front of the opposing face 96. Light reflected by the target object passes through the detection hole 112 and is received by the photoreceptor element. The separation distance sensor 110 corresponds to the distance detection unit of the present invention. The communications controller 108 and the separation distance sensor 110 are connected to a positional change monitoring unit 114. The positional change monitoring unit 114 is also realized by a microcomputer. Details will be explained later, but in general terms the positional change monitoring unit 114 carries out positional change monitoring processing (FIG. 6A and FIG. 6B) in a similar manner to the position change monitoring unit 78 of the electronic cassette 12.

Figure 3C:
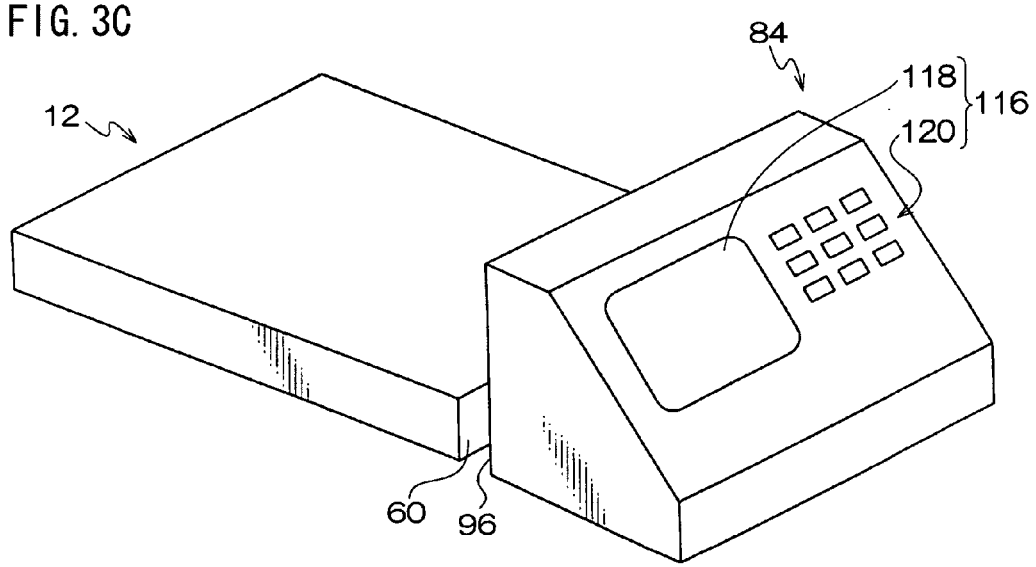

An operation unit 116 is connected to the communications controller 108. The operation unit 116, as shown in FIG. 3B and FIG. 3C, is configured to include a display 118, provided on the casing 94 and capable of displaying given information including various messages, and a keyboard 120 of plural keys, also provided on the casing 94. Various instructions and information are input to the communications controller 108 by a user operating the keyboard 120, and display of information on the display 118 is controlled by the communications controller 108.

An image memory 124 is connected through an image processing unit 122 to the communications controller 108. In communication between the electronic cassette 12 and the image reading device 84, as will be described later, image data stored in the image memory 50 of the electronic cassette 12 is transferred to the image reading device 84, and the image processing unit 122 carries out various image processing (for example various types of correction processing such as removal of noise superimposed on the image data, correcting the variation of the image data by pixel caused by variation in the properties of each of the pixel portions 40 of the radiation detector 26, etc.) on the image data that has been received from the electronic cassette 12 and output in sequence from the communications controller 108. The image data that has been subjected to the various types of image processing is stored in the image memory 124.

An output control unit 126 is connected to the image memory 124. When outputting image data stored in the image memory 124 is output to an external device, the output control unit 126 reads out the image data from the image memory 124 and controls the output of the image data to the external device. A display 128 is shown in FIG. 1 as a typical example of an external device, and when the external device is the display 128 an image represented by the image data stored in the image memory 124 (a radiographic image) is displayed on the display 128 by the output control unit 126. Examples of other external devices, other than the display 128, include for example printing devices for printing an image represented by the image data on a sheet printing medium, information recording devices for recording image data on a CD-R or other known recording medium, communication devices for transmitting image data to an information processing device connected through a communications network, etc.

While the power source of the image reading device 84 is not shown in FIG. 1, the power source is configured by constant connection to a commercial power source, with rectification and voltage transformation of the power supplied from the commercial power source before supplying power to the various circuits and elements within the image reading device 84.

Explanation will now be given of communication between the electronic cassette 12 and the image reading device 84 as operation of the first exemplary embodiment. When it is desired by a user to display image data, stored in the image memory 50 of the electronic cassette 12 by carrying out radiographic imaging, as an image on the display 128, the user disposes the electronic cassette 12 so that the opposing face 60 faces and is aligned with the opposing face 96 of the image reading device 84 (so as to arrive at the state shown in FIG. 3C), in order to read the image data from the electronic cassette 12 using the image reading device 84. After carrying out fine adjustment of the positional arrangement such that each of the end faces are aligned, the user then operates the keyboard 120 of the image reading device 84 to instruct reading out of the image data from the electronic cassette 12.

The communications controller 108 of the image reading device 84 carries out the above operations instructed by the user, and when the image data is instructed to be read out from the electronic cassette 12, the communications controller 108 performs the data readout processing shown in FIG. 4A and FIG. 4B. In this data readout processing, first at step 150 a micro output laser light is emitted from the LD 86 via the modulation unit 104. In the next step 152, determination is made as to whether or not laser light has been received by the PD 90. The routine proceeds to step 154 when determination is made that it has not been received, and determination is made as to whether or not a specific duration has elapsed since starting emitting the laser light from the LD 86. If determination is that the duration has not elapsed the routine returns to step 152, and step 152 and step 154 are repeated until one or other thereof is determined in the affirmative.

The micro output laser light emitted from the LD 86 passes through the emission hole 98 and is emitted out from the casing 94 of the image reading device 84, however this laser light passes through the light receiving hole 64 and is incident into the casing 20 of the electronic cassette 12. When the laser light is detected (sensed) by the PD 56, a micro output laser light is emitted from the LD 52 of the electronic cassette 12, as described later. This laser light should be received by the PD 90, and so if step 154 determines that the specific duration has elapsed since starting to emit the laser light from the LD 86 and yet the laser light has not been received by the PD 90, then it can be concluded that there is displacement of the relative positions of the electronic cassette 12 to the image reading device 84 from the positional relationship enabling communication (the position in which the electronic cassette 12 and the image reading device 84 are each able to receive light from the laser light emitted by the opposing device), and can be concluded that relative positional adjustment is required.

Therefore, when the determination is affirmative at step 154 the emission of the laser light from the LD 86 is stopped at step 190, and at the next step 192, an error message, such as a request to adjust the relative position, is displayed on the display 118. After urging the user to execute relative positional alignment actions, the data readout processing (FIG. 4A and FIG. 4B) is ended. When there is a large displacement in the relative positions of the electronic cassette 12 and the image reading device 84 from the positional relationship enabling communication, there is a possibility that the laser light emitted from the image reading device 84 leaks out from the space interposed between the opposing face 60 of the electronic cassette 12 and the opposing face 96 of the image reading device 84. However, this does not cause a problem since the laser light amount (light intensity) emitted from the LD 86 of the image reading device 84 at this stage is minute.

If the relative positions of the electronic cassette 12 and the image reading device 84 is the positional relationship enabling communication then when the micro output laser light emitted from the image reading device 84 is received as light (detected) by the PD 56 of the electronic cassette 12, the communications controller 72 of the electronic cassette 12 performs the data transfer processing shown in FIG. 5A and FIG. 5B. In this data transfer processing, first at step 200 a micro output laser light is emitted from the LD 52 via the modulation unit 68. The micro output laser light emitted from the LD 52 passes through the emission hole 62 and is emitted out from the casing 20 of the electronic cassette 12. However, when this laser light passes through the light receiving hole 100, is introduced into the casing 94 of the image reading device 84, and is detected (sensed) by the PD 90, the determination of step 152 of the data readout processing (FIG. 4A and FIG. 4B) is affirmative, and the routine proceeds to step 156.

When the determination of this step 152 is affirmative, the micro output laser light emitted from the LD 86 of the image reading device 84 is detected (sensed) by the PD 56 of the electronic cassette 12, and the micro output laser light emitted from the LD 52 of the electronic cassette 12 is also detected (sensed) by the PD 90 of the image reading device 84. Determination is therefore made that the relative position of the electronic cassette 12 and the image reading device 84 is the optimal positional relationship enabling communication, where the laser light emitted from the LD 86 is incident at the center, or in the vicinity of the center, of the light receiving face of the PD 90, and where also the laser light emitted from the LD 52 is incident at the center, or in the vicinity of the center, of the light receiving face of the PD 90.

At the subsequent step 156 of the data readout processing (FIG. 4A and FIG. 4B) and step 202 of the data transfer processing (FIG. 5A and FIG. 51B), opposing device confirmation processing is carried out to determine whether or not opposing device is a normal device. This is accomplished by specific information being transmitted by laser light from the device itself (modulating the laser light emitted from the LD of the device itself according to the specific information), and the contents of information received by laser light from the opposing device (information obtained by demodulating the laser light emitted from the LD of the opposing device and received by the PD of the device itself) being confirmed. An example of the information transmitted by the electronic cassette 12 to the image reading device 84 in opposing device confirmation processing is a cassette ID or the like for discriminating between individual electronic cassettes 12. An example of information transmitted by the image reading device 84 to the electronic cassette 12 is information indicating that the device itself is an image reading device.

Determination is made at the next step 158 in the data readout processing (FIG. 4A and FIG. 4B) as to whether or not the opposing device is a normal device, and if this determination is negative then at step 190 the laser light emitted from the LD 86 is stopped. Next, error processing is carried out at step 192, such as displaying an error message advising that the opposing device is not the normal device on the display 118, and the data readout processing (FIG. 4A and FIG. 4B) is ended. In the data transfer processing (FIG. 5A and FIG. 5B) too, determination is made at the next step 204 as to whether or not the opposing device is the normal device, and if this determination is negative then at step 236 the laser light emitted from the LD 52 is stopped and data transfer processing (FIG. 5A and FIG. 5B) is ended.

In the data readout processing (FIG. 4A and FIG. 4B), when determination is made that the opposing device is the normal device (electronic cassette 12) then determination at step 158 is affirmative and the routine proceeds to step 160, and the value for the laser light output is set to the normal value. Next at step 162, information requesting data transfer from the opposing device is transmitted by laser light to the opposing device. At step 164, instruction is given to the positional change monitoring unit 114 to start execution of the positional change monitoring processing (FIG. 6A and FIG. 6B). Note that this positional change monitoring processing is described later. At step 166, determination is made as to whether or not the data transferred from the opposing device has been received. If determination is negative then the routine proceeds to step 168, and determination is made as to whether completion of data transfer has been notified from the opposing device. If this determination is negative then the routine proceeds to step 170, and determination is made as to whether or not halting of communication with the opposing device has been instructed from the positional change monitoring unit 114. When this determination is negative the routine returns to step 166, and step 166 to step 170 are repeated until one or other determination is affirmative.

In the data transfer processing (FIG. 5A and FIG. 5B), when determination is made that the opposing device is the normal device (image reading device 84) then determination at step 204 is affirmative and the routine proceeds to step 206, determination is made as to whether or not information requesting data transfer from the opposing device has been received, and step 206 is repeated until determination is affirmative. When information requesting data transfer is received by the image reading device 84 carrying out the processing of step 162 of FIG. 4A and FIG. 4B, the determination at step 206 is affirmative and the routine proceeds to step 208, and the value of the laser light output from the LD 52 is set to the value during normal communication. At step 210, instruction is given to the position change monitoring unit 78 to start execution of the positional change monitoring processing (FIG. 6A and FIG. 6B). At the next step 212, trial reading from the image memory 50 of image data that needs to be transferred to the image reading device 84 is carried out.

At the next step 214, determination is made as to whether or not there is image data for transfer (image data not yet transferred to the image reading device 84) stored in the image memory 50. When this determination is affirmative the routine proceeds to step 216, and the image data for transfer generated by reading from the image memory 50 is transmitted to the opposing device (image reading device 84) by laser light. Determination is made at step 218 as to whether or not a response has been received from the image reading device 84. When this determination is negative then the routine proceeds to step 220, and determination is made as to whether or not halting communication with the opposing device has been instructed from the position change monitoring unit 78. When this determination is negative the routine returns to step 218, and step 218 to 220 are repeated until one or other is determined in the affirmative.

When image data is transmitted by laser light from the electronic cassette 12 and this image data is received by the image reading device 84, as described above, the determination of step 166 of the data readout processing (FIG. 4A and FIG. 4B) is made in the affirmative then the routine proceeds to step 172, and the image data received from the opposing device (electronic cassette 12) is output downstream (to the image processing unit 122 in the present exemplary embodiment). The image data received thereby with the image reading device 84 is subjected to various image processing by the image processing unit 122 and is then stored in the image memory 124. In the next step 174 a response to the data transmission by the laser light of the opposing device (electronic cassette 12) is transmitted, and the routine returns to step 166. By receipt of this response by the opposing device (electronic cassette 12) determination is made in the affirmative at step 218 of the data transfer processing (FIG. 5A and FIG. 5B) and the routine returns to step 212. In this manner, step 166 to step 174 of data readout processing (FIG. 4A and FIG. 4B) are repeated for the interval during which the image data for transfer is stored in the image memory 50 of the electronic cassette 12, and image data is transmitted successively to the image reading device 84 by repeating step 212 to step 220 of data transfer processing (FIG. 5A and FIG. 5B).

When all of the image data stored on in the image memory 50 has been sent to the image reading device 84, the determination at step 214 of the data transfer processing (FIG. 5A and FIG. 5B) is negative and the routine proceeds to step 230, where notification of data transfer completion is made by laser light to the opposing device (image reading device 84). At step 232 the laser light emitted from the LD 52 is stopped. Then at step 234 instruction is given to the position change monitoring unit 78 to end positional change monitoring processing (FIG. 6A and FIG. 6B), and data transfer processing (FIG. 5A and FIG. 5B) is ended. When notification of data transfer completion from the electronic cassette 12 is made, the determination at step 168 in the data readout processing (FIG. 4A and FIG. 4B) is negative, the routine proceeds to step 176, and the laser light emitted from the LD 86 is stopped. Instruction is given to the positional change monitoring unit 114 at step 178 to end positional change monitoring processing (FIG. 6A and FIG. 6B), and data readout processing (FIG. 4A and FIG. 4B) is ended.

Explanation will now be given regarding the positional change monitoring processing respectively executed in the position change monitoring unit 78 of the electronic cassette 12 and the positional change monitoring unit 114 in the image reading device 84. In the following explanation the positional change monitoring processing is executed in the first and the second control units according to the present invention.

As explained before, communication between the electronic cassette 12 and the image reading device 84 is commenced when the relative position of the electronic cassette 12 to the image reading device 84 is in the adjusted positional relationship enabling communication state (state shown in FIG. 3A). However, for example, it is possible that during communication the relative position is displaced from the positional relationship enabling communication when the casing 20 of the electronic cassette 12 and/or the casing 94 of the image reading device 84 is imparted with a pressing force, vibration or the like etc. In such cases, the possibility of the laser light emitted from the image electronic cassette 12 and the reading device 84 leaking out from in the space interposed between the opposing face 60 of the electronic cassette 12 and the opposing face 96 of the image reading device 84 is not desirable. Therefore, when communication is commenced between the electronic cassette 12 and the image reading device 84, execution of positional change monitoring processing is started in the position change monitoring units 78, 114, under the instruction from the communications controller of the device itself. The change in relative position between the electronic cassette 12 and the image reading device 84 is monitored by continuously executing the positional change monitoring processing during the period in which communication is being performed between the electronic cassette 12 and the image reading device 84.

Namely, as shown in FIG. 6A and FIG. 6B, first at step 250 in the positional change monitoring processing, the current separation distance (separation distance detection value L) from the device itself to the opposing device, detected by the separation distance sensor of the device itself, is acquired from the separation distance sensor. This is carried out just after the relative position of the electronic cassette 12 and the image reading device 84 has been adjusted to the positional relationship enabling communication, and so the separation distance detection value L represents the separation distance from the disposed position of the separation distance sensor to the casing of the opposing device when the relative position of the electronic cassette 12 and the image reading device 84 has been adjusted to the positional relationship enabling communication state. In the next step 252, the separation distance detection value L acquired in step 250 is stored in an internal memory or the like as a reference value L ref of the separation distance to the opposing device (see FIG. 7A).

Then at step 254, the laser received light amount of the PD detected with the demodulation unit of the device itself (laser received light amount detected value P1) is acquired via the communications controller of the device itself at a timing just after starting data transfer when the PD is receiving light from the laser light. This laser received light amount detected value P1 also represents a laser received light amount of the PD in the positional relationship enabling communication state of relative position between the electronic cassette 12 and the image reading device 84. Appropriate received light amounts to use as the laser received light amount detected value P1 include any of the maximum value of the laser received light amount in the period of time the PD receives light, the average value thereof, and the received light amount at which the cumulative frequency reaches a specific value from the maximum or minimum values on a histogram of the laser received light amount. Another value can also be used therefore as long as it is a value representative of the laser received light amount of the PD in the adjusted state of relative positions between the electronic cassette 12 and the image reading device 84, in the positional relationship enabling communication. In the next step 256 the laser received light amount detected value P1 acquired at step 254 is stored in an internal memory or the like as a laser received light amount reference value P1 ref (see FIG. 8A).

At the next step 258, the current separation distance (separation distance detection value L) from the device itself to the opposing device, detected by the separation distance sensor of the device itself, is again acquired from the separation distance sensor. At the next step 260, determination is made as to whether or not the separation distance detection value L acquired in step 258 is the same as or more than the separation distance reference value L ref to the opposing device plus a specific value $\alpha$ (L$\geq$L ref+$\alpha$). If this determination is negative then it can be concluded that any change in separation distance from the disposed position of the separation distance sensor to the opposing device is within a permissible range, and the routine proceeds to step 262. Here, the latest laser received light amount of the PD detected by the demodulation unit of the device itself (laser received light amount detected value P1) is again acquired via the communications controller of the device itself. Next, at step 264 determination is made as to whether or not the laser received light amount detected value P1 acquired at step 262 is a value the same as or less than the laser received light amount reference value P1 ref minus a specific value $\beta$ (P1$\leq$P1 ref$-\beta$). For the size of the specific value $\beta$, it can be varied according to which of the values given above as examples of the laser received light amount detected value P1 (maximum value, minimum value etc.) is used. If determination at step 264 is negative then it can be concluded that any reduction in the laser received light amount of the PD is within a permissible range, and the routine proceeds to step 266 where determination is made as to whether or not ending of the positional change monitoring processing has been instructed from the communications controller of the device itself. If this determination is negative, then the routine returns to step 258.

Changes in the separation distance detection value L and in the laser received light amount detected value P1 are monitored by the above by repeating step 258 to step 266 until any one of steps 260, 264, or 266 is determined in the affirmative. During the period of time when the electronic cassette 12 and the image reading device 84 are communicating, if there is no change, or only a minute change, in the relative position of the electronic cassette 12 and the image reading device 84, then there is no affirmative determination at steps 260 or 264, and the determination at step 266 is affirmative when ending of positional change monitoring processing is instructed from the communications controller of the device itself, and the positional change monitoring processing is ended.

If the casing 20 of the electronic cassette 12 and/or the casing 94 of the image reading device 84 is imparted with a pressing force, vibration or the like during communication between the electronic cassette 12 and the image reading device 84, and the relative position of the electronic cassette 12 and the image reading device 84 has changed from the state shown in FIG. 7A to the state shown in FIG. 7B (when a comparatively large change in the relative position occurs), then, as shown in FIG. 7B, the laser light emitted from the electronic cassette 12 and the image reading device 84 is greatly displaced from the center of the light receiving face of the PD of the opposing device, resulting in the possibility that the laser light leaks out from the space interposed between the opposing face 60 of the electronic cassette 12 and the opposing face 96 of the image reading device 84.

When there is a relatively large change in the relative position of the electronic cassette 12 and the image reading device 84 then along with this change there is a change in the separation distance between the disposed position of the separation distance sensor and the casing of the opposing device (in the length of the arrows shown with solid lines in FIG. 7B). In the example of FIG. 7B, the separation distance detection value L corresponding to the solid arrow of the two solid arrows positioned at the upper side in the figure is increased by a great amount, and the determination at step 260 is in the affirmative. Changes in the relative position of the electronic cassette 12 and the image reading device 84 which might lead to the possibility of laser light leakage can thereby be detected by monitoring the separation distance detection value L.

The laser received light amount of the PDs changes with changes in the position of the optical axis of the laser light irradiated onto the PD, as shown in FIG. 8C. As the deflection of the position of the optical axis of the laser light from the center position of the light receiving region increases, the attenuation in the laser received light amount of the PD gets greater. When there is a comparatively large change in the relative position of the electronic cassette 12 and the image reading device 84, as shown in FIG. 8B, the incident position of the laser light on the PDs of the electronic cassette 12 and the image reading device 84 is displaced greatly from the center of the light receiving region, and determination at step 264 is affirmative due to the large decrease in the laser received light amount detected value P1. Consequently, changes in the relative position of the electronic cassette 12 and the image reading device 84 which might lead to the possibility of laser light leakage can thereby also be detected by monitoring the laser received light amount detected value P1. When the determination at step 260 or at step 264 is affirmative the routine proceeds to step 268, and after halting communication has been instructed to the communications controller of the device itself, the positional change monitoring processing is ended.

If the positional change monitoring unit 114 of the image reading device 84 instructs the communications controller 108 to halt communication then the determination at step 170 of the data readout processing (FIG. 4A and FIG. 4B) is affirmative and the routine proceeds to step 180 where determination is made as to whether or not halting communication has been instructed from the opposing device. In this example the instruction to halt communication comes from the positional change monitoring unit 114 of the device itself, and so determination is negative and the routine proceeds to step 182, where the opposing device (electronic cassette 12) is instructed by laser to halt communication. In step 186, emission of laser light from the LD 86 is stopped, and at the next step 188, along with stopping communication, error processing is carried out, such as displaying on the display 118 an error message notifying the reason for stopping (that the casing has moved by a large extent), and data readout processing (FIG. 4A and FIG. 4B) is ended. In the electronic cassette 12 instructed from the image reading device 84 to halt communication, determination at step 220 of the data transfer processing (FIG. 5A and FIG. 5B) is affirmative and the routine proceeds to step 222, where determination is made as to whether halting communication is instructed from the opposing device. In this example this determination is affirmative, and the routine proceeds to step 226, and ending of positional change monitoring processing (FIG. 6A and FIG. 6B) is instructed to the position change monitoring unit 78. Then at step 228 the emission of the laser light from the LD 52 is stopped and the data transfer processing (FIG. 5A and FIG. 5B) is ended.

If the position change monitoring unit 78 of the electronic cassette 12 has instructed the communications controller 72 to halt communication then the determination of step 220 of the data transfer processing (FIG. 5A and FIG. 5B) is affirmative and the determination at face 222 is negative, and the routine proceeds to step 224 where the opposing device (image reading device 84) is instructed by laser light to halt communication. At step 228 the emission of laser light from the LD 52 is stopped, and the data transfer processing (FIG. 5A and FIG. 5B) is ended. In the image reading device 84 instructed from the electronic cassette 12 to halt communication, at step 184 the positional change monitoring unit 114 is instructed to end positional change monitoring processing (FIG. 6A and FIG. 6B). At step 186 the emission of the laser light from the LD 86 is stopped, and at step 188 the error processing described above is performed and the data readout processing (FIG. 4A and FIG. 4B) is ended.

When a change in the relative position of the electronic cassette 12 and the image reading device 84 possibly leading to laser light leakage is detected by one or other of the position change monitoring unit 78 of the electronic cassette 12 and/or with the positional change monitoring unit 114 of the image reading device 84, then the laser light being emitted from the electronic cassette 12 and the laser light being emitted from the image reading device 84 are each stopped.

Also in the first exemplary embodiment, a portion of the region at the periphery of the light receiving hole 64 (and the emission hole 62) of the opposing face 60 of the casing 20 of the electronic cassette 12 is covered by diffusing material 66, and a portion of the region at the periphery of the light receiving hole 100 (and the emission hole 98) of the opposing face 96 of the casing 94 of the image reading device 84 is covered by diffusing material 102. As a result, in the interval during communication between when a relatively large change occurs in the relative position of the electronic cassette 12 and the image reading device 84 up until the laser light emission is stopped by the above processing, even if a state temporarily occurs in which the laser light emitted from the electronic cassette 12 and the image reading device 84 is irradiated at a position outside of the light receiving hole in the opposing face of the opposing device, the laser light irradiated on the opposing face of the opposing device is reflected in various mutually different plural directions by the diffusing material provided at the irradiated position of the laser light, and so the reflected light is diffused. Therefore even in cases where the reflected laser light leaks out from the space interposed between the opposing face 60 of the electronic cassette 12 and the opposing face 96 of the image reading device 84, the amount of light of the laser light irradiated to a particular position outside of this space can be made to be extremely weak.

Second Exemplary Embodiment

Explanation will now be given of a second exemplary embodiment of the present invention. Portions similar to those of the first exemplary embodiment are allocated the same reference numerals and explanation thereof is omitted. The second exemplary embodiment differs from the first exemplary embodiment in that, as shown in FIG. 9, a peripheral light sensor 130 is provided to the electronic cassette 12, and a peripheral light sensor 132 is provided to the image reading device 84.

As shown in FIG. 10A, the peripheral light sensor 130 provided to the electronic cassette 12 has a detection region 130A of a circular ring shape around the periphery of the light receiving hole 64 on the opposing face 60 of the casing 20 of the electronic cassette 12. There are plural individual photoelectric converting elements provided within the detection region 130A, formed from uniformly distributed PDs or the like. The photoelectric converting elements used as the photoelectric converting elements configuring the peripheral light sensor 130 are those which have spectral sensitivity characteristics with sensitively to the laser light emitted from the LD 86 of the image reading device 84. The peripheral light sensor 130 is connected to the position change monitoring unit 78, and outputs to the position change monitoring unit 78, for example, a signal corresponding to the total received light amount by the plural individual photoelectric converting elements, or to the maximum received light amount of the individual photoelectric converting elements. In the second exemplary embodiment, the diffusing material 66 provided to the opposing face 60 is provided to the disposed range on the opposing face 60 explained in the first exemplary embodiment, except for the range occupied by the detection region 130A.

As shown in FIG. 10B, the peripheral light sensor 132 provided to the image reading device 84 has a detection region 132A of a circular ring shape around the periphery of the light receiving hole 100 on the opposing face 96 of the casing 94 of the image reading device 84. There are plural individual photoelectric converting elements provided within the detection region 132A, formed from uniformly distributed PDs or the like. Photoelectric converting elements used as the photoelectric converting elements configuring the peripheral light sensor 132 are those which have spectral sensitivity characteristics with sensitively to the laser light emitted from the LD 52 of the electronic cassette 12. The peripheral light sensor 132 is connected to the position change monitoring unit 114, and outputs to the position change monitoring unit 114, for example, a signal corresponding to the total received light amount by the plural individual photoelectric converting elements, or to the maximum received light amount of the individual photoelectric converting elements. Note that the diffusing material 66 provided to the opposing face 96 is provided to the disposed range on the opposing face 96 explained in the first exemplary embodiment, except for in the range occupied by the detection region 132A.

Explanation will now be given of portions of the positional change monitoring processing carried out by the position change monitoring units 78, 114 according to the second exemplary embodiment differing from the first exemplary embodiment, with reference to FIG. 11A and FIG. 11B. The positional change monitoring processing according to the second exemplary embodiment, in place of detecting changes in the relative position of the electronic cassette 12 and the image reading device 84 based on the received light amount of the PDs, detects the relative position of the electronic cassette 12 and the image reading device 84 based on the received light amount of the peripheral light sensors 130, 132.

Namely, in the positional change monitoring processing according to the second exemplary embodiment, the separation distance detection value L is acquired from the separation distance sensor (step 250), then after storing the acquired separation distance detection value L as the separation distance reference value L ref (step 252), in step 255, the laser received light amount detected by the peripheral light sensor provided to the device itself (laser received light amount detected value P2) is acquired from the peripheral light sensor, at a timing just after commencing data transfer when laser light is being received by the PD. Since this time is just after the relative position of the electronic cassette 12 and the image reading device 84 has been adjusted to the positional relationship enabling communication, the laser received light amount detected value P2 acquired in step 255 represents the received light amount of the laser light with the peripheral light sensor in the adjusted state of the relative position of the electronic cassette 12 and the image reading device 84, in the positional relationship enabling communication.

Appropriate received light amounts to use as the laser received light amount detected value P2 include any of the maximum value of the laser received light amount by the peripheral light sensor in the period of time the PD receives light, the average value thereof, and the received light amount at which the cumulative frequency reaches a specific value from the maximum or minimum values on a histogram of the laser received light amount. Another value can also be used as long as it is a value representative of the laser received light amount by the peripheral light sensor in the adjusted state of the relative position between the electronic cassette 12 and the image reading device 84, in the positional relationship enabling communication. In the next step 257 the laser received light amount detected value P2 acquired at step 255 is stored in an internal memory or the like as laser received light amount reference value P2 ref (see FIG. 12A) of the peripheral light sensor.

In the positional change monitoring processing according to the second exemplary embodiment, the separation distance detection value L is reacquired from the separation distance sensor (step 258), if the reacquired separation distance detection value L does not satisfy "L≧L ref+α" (when there is a negative determination at step 260) then the latest laser received light amount of the peripheral light sensor (laser received light amount detected value P2) of the device itself is reacquired at step 263. Next, at step 265 determination is made as to whether or not the laser received light amount detected value P2 acquired at step 263 is a value the same as or greater than the laser received light amount reference value P2 ref plus a specific value γ (P2≧P2 ref+γ). The size of the specific value γ can also be varied according to the application, together with which of the values given above as examples of the laser received light amount detected value P2 (maximum value, minimum value etc.) is used. If determination at step 265 is negative then it can be concluded that any increase in the laser received light amount by the peripheral light sensor is within a permissible range, and the routine proceeds to step 266.

Changes in the separation distance detection value L and in the laser received light amount detected value P2 are monitored in the above manner by repeating step 258 to step 266 for the period of time when the electronic cassette 12 and the image reading device 84 are communicating. If there is no change, or only a minute change, in the relative position of the electronic cassette 12 and the image reading device 84 during this period, then there is no affirmative determination at step 265 (and step 260), since there is no change in the separation distance detection value L or in the laser received light amount detected value P2, or there is only a minute change therein. The positional change monitoring processing is ended when instruction to end positional change monitoring processing is given from the communications controller of the device itself.

If the position of the optical axis of the laser light incident on the PD has changed, then as the amount of deflection of the optical axis position of the laser light relative to the central position of the light receiving region increases, the laser received light amount of the peripheral light sensor changes by first showing an increase to a peak value, and then by showing a decrease as the deflection amount increases further, as shown in FIG. 12C. If during communication between the electronic cassette 12 and the image reading device 84 the casing 20 of the electronic cassette 12 and/or the casing 94 of the image reading device 84 is imparted with a pressing force, vibration or the like, and the relative position of the electronic cassette 12 and the image reading device 84 changes from the state shown in FIG. 12A to the state shown in FIG. 12B (when a comparatively large change in the relative position occurs), then, as shown in FIG. 12B, the incident positions on the PDs of the laser light emitted from the electronic cassette 12 and the image reading device 84 are greatly displaced from the center of the light receiving regions, and determination at the previous step 265 is affirmative due to the large increase in the laser received light amount detected value P2.

When there is an even greater change in the relative position of the electronic cassette 12 and the image reading device 84 then, as is clear from FIG. 12C, the change in the laser received light amount detected value P2 changes to a decrease after increasing to the maximum value. However, the initial relative position of the electronic cassette 12 and the image reading device 84 is the adjusted positional relationship shown in FIG. 12A, and since change in the laser received light amount detected value P2 is constantly monitored during execution of positional change monitoring processing, the increase in the laser received light amount detected value P2 is detected during the period from when the laser received light amount detected value P2 increases up to the maximum value thereof along with the deflection of the optical axis position of the laser light, and determination at step 265 is affirmative. Therefore changes in the relative position of the electronic cassette 12 and the image reading device 84 possibly leading to laser light leakage are also detectable by monitoring the laser received light amount detected value P2.

A mode has been explained in which a portion of the region at the periphery of the light receiving hole 64 (and the emission hole 62) of the opposing face 60 of the casing 20 of the electronic cassette 12, and a portion of the region at the periphery of the light receiving hole 100 (and the emission hole 98) of the opposing face 96 of the casing 94 of the image reading device 84, are covered by diffusing materials 66, 102. However there is no limitation thereto, and in place of the diffusing material, covering may be made with an absorbing material for absorbing most of the laser light irradiated thereon (for example a selective wavelength optical filter (more precisely a light absorbing filter with light absorbance to the wavelength region of the irradiated laser light)), a furry material or porous material, a member with a black surface, etc.). There are, for example, commercially available light absorbing filters configured with light absorbing substances dispersed within glass and having a transmittance of about 20% to light of 1300 nm wavelength, from laser light that is suitably applied for communication between the electronic cassette 12 and the image reading device 84. It is possible to achieve a light absorbing material capable of suppressing reflected light to a few % of the incident light by using such a light absorbing filter and giving an anti-reflection coating treatment to the surface of such a light absorbing filter to suppress any surface light reflection.

Relatively large changes in the relative position of the electronic cassette 12 and the image reading device 84 can also occur during communication when an absorbing material is provided in place of the diffusing material. For the period of time up to when the change in the relative position is detected and the emission of the laser light is stopped, in the temporary state that occurs where the laser light emitted from the electronic cassette 12 and the image reading device 84 is irradiated to a position on the opposing face of the opposing device outside of the light receiving hole, the laser light irradiating onto a position outside of the light receiving hole is irradiated onto the absorbing material. Most of the laser light is thereby absorbed by the absorbing material, and the amount of light of laser light leaking out from the space interposed between the opposing face 60 of the electronic cassette 12 and the opposing face 96 of the image reading device 84 can be made to be extremely weak.

When a non-visible laser light with a wavelength outside of the visible region is used for communication between the electronic cassette 12 and the image reading device 84, a light emitting (luminescent) material may be used as a covering in place of the diffusing materials 66, 102 on a portion of the above described region, so that light in a visible region is emitted from portions on which the non-visible laser light is irradiated. For example, if the laser light has a wavelength in the infrared region then a light path confirmation luminescent sheet (LASER DETECTION CARD IR) for near infrared made by Edmund Optics may be used as the above light emitting (luminescent) material.

When a light emitting (luminescent) material is used in place of the diffusing material, as described above, a reduction of laser light amount effect similar to that of diffusing materials and absorbing materials is not obtained. When relatively large changes in the relative position of the electronic cassette 12 and the image reading device 84 occur during communication, for the period of time up to when the change in the relative position is detected and the emission of the laser light is stopped, in the temporary state that occurs where the non-visible laser light emitted from the electronic cassette 12 and the image reading device 84 is irradiated to a position on the opposing face of the opposing device outside of the light receiving hole, the non-visible laser light irradiating onto a position outside of the light receiving hole is irradiated onto the light emitting (luminescent) material and light is emitted (visible light is emitted) from light emitting (luminescent) material onto which the non-visible laser light is irradiated. As a result a user is able to confirm that the irradiation position of the non-visible laser light is outside of the light receiving hole, and is able to confirm that there is possibility that the non-visible laser light is leaking out from the space interposed between the opposing face 60 of the electronic cassette 12 and the opposing face 96 of the image reading device 84. It is therefore possible for a user to take counter measures to avoid the leaking non-visible laser light from irradiating onto specific locations outside of this space (locations where it is not desirable for the laser light to be irradiated).

In the positional change monitoring processing of FIG. 6A and FIG. 6B and FIG. 11A and FIG. 11B only the increase in the separation distance detection value L is monitored, however there is no limitation thereto and monitoring may be combined with monitoring of reductions in the separation distance detected value (for example whether or not L≦Lref−α).

In addition, explanation has been given above for the above separation distance sensors 74, 110 of a configuration that detects the separation distance to the target object based on the time from emitting light from a light emitting element until the emitted light is reflected from the target object and received by a photoreceptor element, however there is no limitation thereto. Configuration may be made in which the position of light receipt when light emitted from a light emitting element is reflected from a target object and received by a photoreceptor element is detected, and the separation distance to the target object is detected using the principals of trigonometry based on the detected position of light receipt. Or a configuration may be made in which an electric field generating unit for generating an electric field of a certain intensity, or a magnetic field generating unit for generating an magnetic field of a certain intensity, is provided on the opposing device side. A configuration may then be used in which the separation distance to a target object is then detected based on the detected intensity of the electric field or the magnetic field generated by the electric field generating unit or the magnetic field generating unit on the opposing device side.

A separation distance detection unit should be configured so as to detect or estimate whether or not there is a change in separation distance to the opposing device of a threshold value or above, and is not limited to a configuration that detects the separation distance to the opposing device. For example when the devices carrying out communication by laser light with each other are configured to carry out communication by laser light when in a state of contact with the opposing device, or when in a state of extremely close proximity to the opposing device, then a configuration may be used provided with a movable member and a displacement detection unit for detecting displacement of the movable member (such as, for example, a limit switch or the like) for a separation distance detection unit. When the devices carrying out communication by laser light with each other are carrying out communication by laser light when in a state of contact with the opposing device, or when in a state of extremely close proximity to the opposing device, then a separation distance detection unit (limit switch or the like) is disposed on the casing (housing) of the opposing device so that the moveable member is in contact and displaces. Whether or not there is a state in which there is no displacement of the moveable member is then detected by the displacement detection unit. Namely, configuration is made so as to detect whether or not there has been a change in the separation distance to the opposing device sufficient (at a threshold value or above) to change the state of displacement of the moveable member.

In addition, when carrying out communication by laser light between the devices, configuration may be made with provision of a wireless communication unit that carries out wireless communication using electromagnetic waves other than those of laser light. When wireless communication with this wireless communication unit is limited by the communicable separation distance between the devices and the positional relationship between the devices, or when there is a communication format (for example wireless communication based on IrDA standards using infrared) where the quality of communication changes greatly depending on the separation distance between the devices and the positional relationship between the devices, information, such as the intensity of the electromagnetic waves from the opposing device, the error rate of wireless communication (for example the frequency of retransmission of information requested to the opposing device, the frequency of corrections to the received information, etc.), or other information detected by the wireless communication unit during wireless communication may be acquired. The separation distance detection unit may then be configured to estimate whether or not there has been a change in the separation distance to the opposing device (positional relationship to the opposing device) of an amount (threshold value or above) that influences the intensity of the electromagnetic waves or error rate of wireless communication based on results of comparison of the acquired information against specific value(s).

In addition a separation distance sensor may be provided to only one of the device itself or to the opposing device carrying out communication by laser. Same applies to cases in which communication of information is carried out by the one device emitting laser light from the device itself or the opposing device, with the other of the two devices using a separate communication means (for example infrared rays or the like) for carrying out transmission of information. In such cases, when it is detected or estimated that the separation distance between the devices has become larger than the specific value by the separation distance detection unit provided to only one of the device itself or the opposing device, the device on the side provided with the separation distance detection unit performs processing to instruct the device on the side not provided with the separation distance detection unit to halt communication (to halt laser light emission), (if the device on the side not provided with the separation distance detection unit is not configured to emit laser light then this processing is not required). The device on the side provided with the separation distance detection unit also performs processing to halt emission of the laser light from the device itself, (if the device on the side provided with the separation distance detection unit is not configured to emit laser light then this processing is not required).

In addition, the first exemplary embodiment combines the laser received light amount detected value P1 of the PD with the separation distance detection value L to detect a change in the relative position of the electronic cassette 12 and the image reading device 84, and the second exemplary embodiment combines the laser received light amount detected value P2 of the peripheral light sensor with the separation distance detection value L. However the present invention is not limited thereto. Change in the relative position may be detected using all of the separation distance detection value L, the laser received light amount detected value P1 of the PD, and the laser received light amount detected value P2 of the peripheral light sensor, or change in the relative position may also be detected using only the separation distance detection value L.

A mode has been described in which, in the positional change monitoring processing by the positional change monitoring unit of the device itself as described above, when a comparatively large change in the relative position of the electronic cassette 12 and the image reading device 84 is detected with a possibility of this leading to laser light leakage, the emission of the laser light from the opposing device is halted by instructing the opposing device to halt communication. However there is no limitation thereto, and configuration may be made in which, for periods without any particular abnormalities, the device itself periodically transmits specific information to the opposing device (this information being usable as a substitute to a normal reply to information transmitted from the opposing device), and information transmission being carried out by laser light for periods of time when this specific information is received. Configuration is made so as to halt emission of the laser light from the opposing device by halting transmission of this specific information to the opposing device when a relatively large change is detected in the relative position. In such cases the period of time from detecting a comparatively large change in the relative position up to when emission of the laser light of the opposing device is halted depends on the interval between transmitting the specific information, and so configuration is preferably made with as short an interval as possible between the specific information.

In addition, explanation has been given of a mode, in the first exemplary embodiment and the second exemplary embodiment of embodiments, where the emission is halted of each of the respective laser light emitted from the electronic cassette 12 and the image reading device 84 when a comparatively large change in the relative position of the electronic cassette 12 and the image reading device 84 with a possibility of leading to laser light leakage is detected by use of positional change monitoring processing by the positional change monitoring unit. There is however no limitation thereto, and configuration may be made in which one or more warnings are given to a user by, for example, a buzzer being sounded, or a warning message being displayed on the display 118, in order to attract the attention of the user, and configuration may be made in which emission of the laser light is halted as well as outputting a warning. Such modes also correspond to the first control unit and the second control unit of the present invention.

Explanation has been given of a mode in which the electronic device according to the present invention described above is the electronic cassette 12 and the image reading device 84, and modes of communication are performed by emitting respective laser light. However configuration may be made in which information transmission is carried out by emission of laser light from one of the communicating devices, with the other of the communicating devices carrying out information transmission with another communications means (for example by infrared rays or the like). In such a case, in consideration of the fact that wireless communication using infrared laser light is executed at extremely high transmission speeds, it is preferable to select the device that transmits large amounts of information as the device transmitting information by laser light emission (for example in the case of an electronic cassette and an image reading device, the electronic cassette transmitting the image data should be selected).

Explanation has been given of the electronic cassette 12 (transportable radiographic imaging conversion device) and image reading device 84 as preferable examples of the electronic device according to the present invention, however the present invention is not limited thereto and the present invention is applicable to any electronic device carrying out wireless communication with another device. In particular, in consideration of the fact that wireless communication using infrared laser light is executed at extremely high transmission speeds, one of the devices is preferably transportable, and the electronic device preferably transmits or receives large amounts of data by wireless communication, or has exacting requirements with respect to transmission or receipt of large amounts of data. Examples of electronic devices according to the present invention include application to imaging devices, such as digital still cameras or digital video cameras, and to equipment that receives still image data or video image data from such imaging devices, such as PCs and printers, with wireless communication carried out by laser light therebetween. Examples of electronic devices according to the present invention include application to portable scanners, and to equipment that receives still image data from such scanners, such as PCs and printers, with wireless communication carried out by laser light therebetween. Examples of electronic devices according to the present invention include application to portable devices provided with at least one function for imaging still images or video images or for reproducing music (for example a portable phone or PDA), with wireless communication carried out by laser light used between such portable devices to exchange image data and music data.

What is claimed is:
1. An electronic device comprising:
   a receiving device, receiving transmission information from an opposing device by detecting laser light emitted from the opposing device, the opposing device provided with a first emission unit for emitting laser light and with a first modulating unit for modulating the laser light emitted from the first emission unit according to the transmission information, and by demodulating the transmission information from the detection result of the laser light;
   a separation distance detection unit, determining whether or not there has been a change in the separation distance to the opposing device of a threshold value or above; and
   a first control unit, issuing a warning or halting emission of the laser light from the opposing device when determination is made by the separation distance detection unit that the separation distance to the opposing device has changed by the threshold value or above.

2. The electronic device of claim 1, wherein the relative position of a casing of the opposing device and a casing of the electronic device is in an adjusted state to a position enabling communication in which the laser light emitted from the first emission unit of the opposing device is incident within a light receiving region provided on an external face of a casing of the electronic device.

3. The electronic device of claim 1, further comprising a wireless communication unit that carries out wireless communication with the opposing device using electromagnetic waves other than those of laser light, wherein the determination by the separation distance detection unit includes estimating whether or not during wireless communication with the opposing device by the wireless communication unit the separation distance to the opposing device has changed by the threshold value or above based on at least one of the intensity of the electromagnetic field from the opposing device detected by the wireless communication unit, and/or an error rate detected in wireless communication by the wireless communication unit.

4. The electronic device of claim 1, wherein: the separation distance detection unit comprises a detection section for detecting at least one of light emitted from a light emitting section provided at the separation distance detection unit and reflected by the casing of the opposing device, and/or an electric field or a magnetic field generated by an electromagnetic field generating section provided to the casing of the opposing device; and the determination as to whether or not the separation distance to the opposing device has changed by the threshold value or above is based on detection by the detection section of the amount of reflected light, the irradiation position of the reflected light, the strength of the electric field, and/or the strength of the magnetic field.

5. The electronic device of claim 1, wherein: the separation distance detection unit comprises a moveable member provided so as to contact the casing of the opposing device and to displace when the relative position of the casing of the opposing device and a casing of the electronic device is in an adjusted state to a position enabling communication, and a displacement detection section for detecting displacement of the moveable member; and the determination as to whether or not the separation distance to the opposing device has changed by the threshold value or above is based on the detected state of displacement of the moveable member by the displacement detection section.

6. The electronic device of claim 1, further comprising a first transmission unit capable of transmitting information to the opposing device, wherein the first control unit halts emission of the laser light from the opposing device by transmitting instruction information instructing halting of laser light emission to the opposing device using the first transmission unit.

7. The electronic device of claim 6, further comprising a second transmission unit for periodically transmitting specific information to the opposing device during period(s) when the receiving device is receiving transmission information normally from the opposing device, wherein the opposing device is configured to emit laser light modulated according to the transmission information from the first emission unit during the period in which the specific information is being periodically received, the first control unit halts emission of the laser light from the opposing device by halting transmission of the specific information to the opposing device by the second transmission unit.

8. The electronic device of claim 1, further comprising a second emission unit for emitting laser light and a second modulating unit for modulating the laser light emitted from the second emission unit according to transmission information, the electronic device being configured for carrying out two-way communication with the opposing device by laser light, wherein when the first control unit halts emission of the laser light from the opposing device, emission of the laser light from the second emission unit is also halted.

9. The electronic device of claim 1, wherein the laser light has a wavelength outside of the visible region.

10. The electronic device of claim 1, wherein the laser light has a wavelength in the infrared region.

11. The electronic device of claim 1, wherein the electronic device is one or other of an imaging device, a portable information device, a transportable radiographic imaging conversion device, or an image read-out device for reading out image information from a transportable radiographic imaging conversion device.

12. An electronic device comprising:
a first emission unit for emitting laser light;
a first modulating unit for modulating the laser light emitted from the first emission unit according to transmission information, wherein the laser light emitted from the first emission unit is detected by a receiving device of an opposing device, and the transmission information is received by demodulation of the transmission information from the detection result of the laser light;
a separation distance detection unit, determining whether or not there has been a change in the separation distance to the opposing device of a threshold value or above; and
a control unit, issuing a warning and/or halting emission of the laser light from the opposing device when determination is made by the separation distance detection unit that the separation distance to the opposing device has changed by a threshold value or above.

13. The electronic device of claim 12, further comprising a wireless communication unit that carries out wireless communication with the opposing device using electromagnetic waves other than those of laser light, wherein: the determination by the separation distance detection unit includes estimating whether or not during wireless communication with the opposing device by the wireless communication unit the separation distance to the opposing device has changed by the threshold value or above based on at least one of the intensity of the electromagnetic field from the opposing device detected by the wireless communication unit, and/or an error rate detected in wireless communication by the wireless communication unit.

14. The electronic device of claim 12, wherein: the separation distance detection unit comprises a detection section for detecting at least one of light emitted from a light emitting section provided at the separation distance detection unit and reflected by the casing of the opposing device, and/or an electric field or a magnetic field generated by an electromagnetic field generating section provided to the casing of the opposing device; and the determination as to whether or not the separation distance to the opposing device has changed by the threshold value or above is based on the detection by the detection section, of the amount of reflected light, the irradiation position of the reflected light, the strength of the electric field, and/or the strength of the magnetic field.

15. The electronic device of claim 12, wherein: the separation distance detection unit comprises a moveable member provided so as to contact the casing of the opposing device and to displace when the relative position of the casing of the opposing device and a casing of the electronic device is in an adjusted state to a position enabling communication, and a displacement detection section for detecting displacement of the moveable member; and the determination as to whether or not the separation distance to the opposing device has changed by the threshold value or above is based on the detected state of displacement of the moveable member by the displacement detection section.

16. The electronic device of claim 12, wherein the opposing device further comprises a second emission unit for emitting laser light and a second modulating unit for modulating the laser light emitted from the second emission unit according to transmission information, and the opposing device is configured for carrying out two-way communication with the electronic device by laser light, and when the control unit halts emission of the laser light from the first emission unit of the electronic device, emission of the laser light from the second emission unit of the opposing device is also halted by transmitting, as the transmission information, instruction information instructing halting of the emission of the laser light from the second emission unit, or by transmitting the instruction information by a third transmission unit capable of transmitting information to the opposing device.

17. The electronic device of claim 12, wherein the laser light has a wavelength outside of the visible region.

18. The electronic device of claim 12, wherein the laser light has a wavelength in the infrared region.

19. The electronic device of claim 12, wherein the electronic device is one or other of an imaging device, a portable information device, a transportable radiographic imaging conversion device, or an image read-out device for reading out image information from a transportable radiographic imaging conversion device.

20. The electronic device of claim 12, wherein the relative position of a casing of the opposing device and a casing of the electronic device is in an adjusted state to a position enabling communication in which the laser light emitted from the first emission unit is incident within a light receiving region provided on an external face of the casing of the opposing device.

* * * * *